(12) United States Patent
Bau et al.

(10) Patent No.: US 11,118,206 B2
(45) Date of Patent: Sep. 14, 2021

(54) MULTIPLE STAGE ISOTHERMAL ENZYMATIC AMPLIFICATION

(71) Applicant: THE TRUSTEES OF THE UNIVERSITY OF PENNSYLVANIA, Philadelphia, PA (US)

(72) Inventors: Haim H. Bau, Swarthmore, PA (US); Michael G. Mauk, Philadelphia, PA (US); Jinzhao Song, Philadelphia, PA (US); Changchun Liu, Bala Cynwyd, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 277 days.

(21) Appl. No.: 16/068,560

(22) PCT Filed: Jan. 13, 2017

(86) PCT No.: PCT/US2017/013403
§ 371 (c)(1),
(2) Date: Jul. 6, 2018

(87) PCT Pub. No.: WO2017/123921
PCT Pub. Date: Jul. 20, 2017

(65) Prior Publication Data
US 2019/0017084 A1  Jan. 17, 2019

Related U.S. Application Data

(60) Provisional application No. 62/278,095, filed on Jan. 13, 2016.

(51) Int. Cl.
*C12Q 1/68* (2018.01)
*C12P 19/34* (2006.01)
(Continued)

(52) U.S. Cl.
CPC ............ *C12P 19/34* (2013.01); *C12Q 1/6846* (2013.01); *C12Q 1/6848* (2013.01);
(Continued)

(58) Field of Classification Search
None
See application file for complete search history.

(56) References Cited

U.S. PATENT DOCUMENTS

2012/0258456 A1  10/2012  Armes et al.
2013/0330777 A1  12/2013  Zhang et al.

FOREIGN PATENT DOCUMENTS

WO   WO-2016100196 A1 *  6/2016   ............... C12Q 1/68

OTHER PUBLICATIONS

Nixon et al. (Biomolecular Detection and Quantification, 2014, 2:4-10) (Year: 2014).*

(Continued)

*Primary Examiner* — Stephanie K Mummert
(74) *Attorney, Agent, or Firm* — BakerHostetler

(57) ABSTRACT

Disclosed herein are methods for multiple stage isothermal amplification of nucleic acid comprising a first substantially isothermal amplification reaction on the nucleic acid to generate a first amplification product and at least one substantially isothermal amplification reaction on the first amplification product to generate at least one second amplification product in an amount sufficient for recovery, testing, or characterization.

20 Claims, 18 Drawing Sheets

Specification includes a Sequence Listing.

(51) Int. Cl.
  *C12Q 1/70* (2006.01)
  *C12Q 1/6893* (2018.01)
  *C12Q 1/6844* (2018.01)
  *C12Q 1/6848* (2018.01)

(52) U.S. Cl.
  CPC .......... *C12Q 1/6893* (2013.01); *C12Q 1/702* (2013.01); *C12Q 1/703* (2013.01)

(56) References Cited

OTHER PUBLICATIONS

Rohrmann et al. (Rice University Thesis, May 2015, p. 1-176) (Year: 2015).*
Teoh et al. (J Clin Microbiol, 2015, 53, No. 3, p. 830-837) (Year: 2015).*
Vincent et al., Helicase-dependent isothermal DNA amplification, EMBO Reports, 2004, 5, 795-800.
Rosser, A., Rollinson, D., Forrest, M. & Webster, B. L. Isothermal Recombinase Polymerase amplification (RPA) of Schistosoma haematobium DNA and oligochromatographic lateral flow detection. Parasit Vectors 8, 446 (2015).
Poole, C.B., Tanner, N. A., Zhang, Y.H., Evans, T.C. & Carlow, C.K.S. Diagnosis of Brugian Filariasis by Loop-Mediated Isothermal Amplification. Plos Neglected Tropical Diseases 6 (2012), 9 pages.
Polley, S.D. et al. Mitochondrial DNA Targets Increase Sensitivity of Malaria Detection Using Loop-Mediated Isothermal Amplification. Journal of Clinical Microbiology 48, 2866-2871 (2010.

Piepenburg et al. "DNA Detection Using Recombination Proteins," PLoS Biology, Jun. 13, 2006 (Jun. 13, 2006), vol. 4, Iss. 7, e204, pp. 1115-1121.
Perkasa, A. et al. Isolation of Zika Virus from Febrile Patient, Indonesia. Emerg Infect Dis 22, 924-925 (2016).
Notomi et al., Loop-mediated isothermal amplification of DNA, Nucleic Acid Research, 2000, 28, e63.
Liu, C. et al. A high-efficiency superhydrophobic plasma separator. 2016, Lab Chip 16, 553-560.
Gandasegui, J. et al. The Rapid-Heat LAMPellet Method: A Potential Diagnostic Method for Human Urogenital Schistosomiasis. Plos Neglected Tropical Diseases 9 (2015).
Fernandez-Soto, P. et al. A Loop-Mediated Isothermal Amplification (LAMP) Assay for Early Detection of Schistosoma ansoni in Stool Samples: A Diagnostic Approach in a Murine Model. Plos Neglected Tropical Diseases 8 (2014).
Euler et al. "Recombinase Polymerase Amplification Assay for Rapid Detection of Rift Valley Fever Virus," Journal of Clinical Virology, Aug. 31, 2012 (Aug. 31, 2012), vol. 54, pp. 308-312.
Crannell et al. "Equipment-Free Incubation of Recombinase Polymerase Amplification Reactions Using Body Heat," PLoS One, Nov. 5, 2014 (Nov. 5, 2014), vol. 9, e112146, pp. 1-7.
Compton et al., Nucleic acid sequence-based amplification, Nature, 1991, 350, 91-92.
Cardoso et al. "Visual Detection of Turkey Coronavirus RNA in Tissues and Feces by Reverse-Transcription Loop-Mediated Isothermal Amplification (RT-LAMP) with Hydroxynaphthol Blue Dye," Molecular and Cellular Probes, Dec. 31, 2010 (Dec. 31, 2010), vol. 24, pp. 415-417.
Blanco et al., Highly Efficient DNA Synthesis by the Phage 429 DNA Polymerase, J. Biol. Chem., 1989, 264, 8935-8940.

* cited by examiner

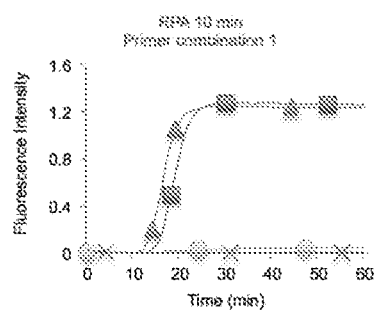 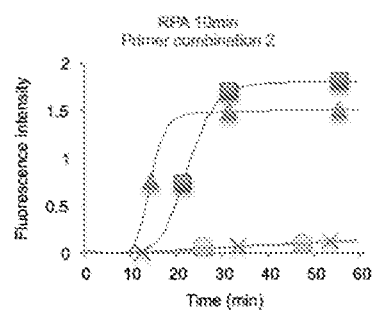 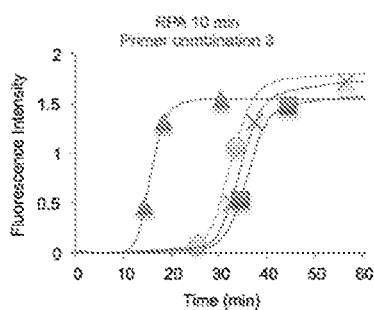
FIG. 7A  FIG. 7B  FIG. 7C
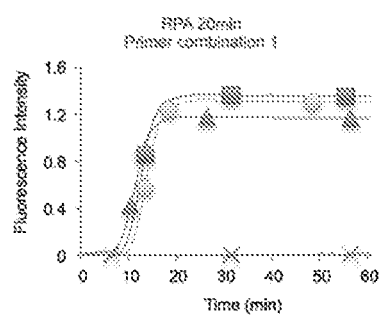 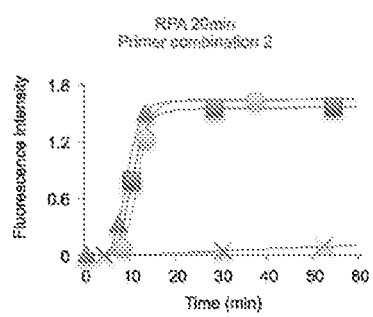 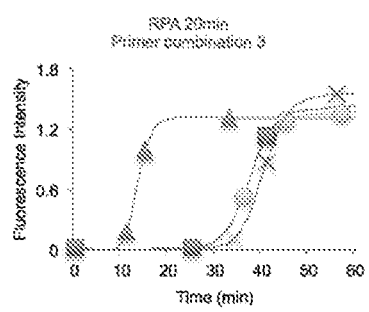
FIG. 7D  FIG. 7E  FIG. 7F

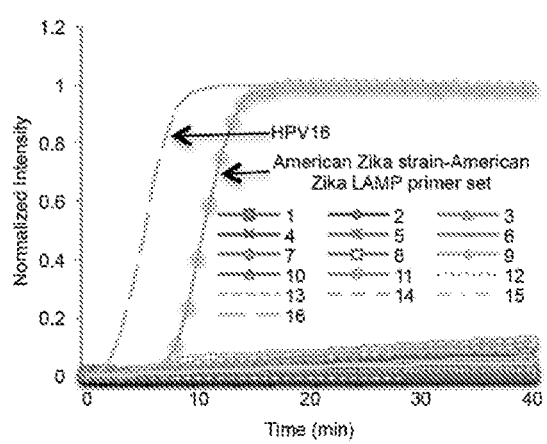
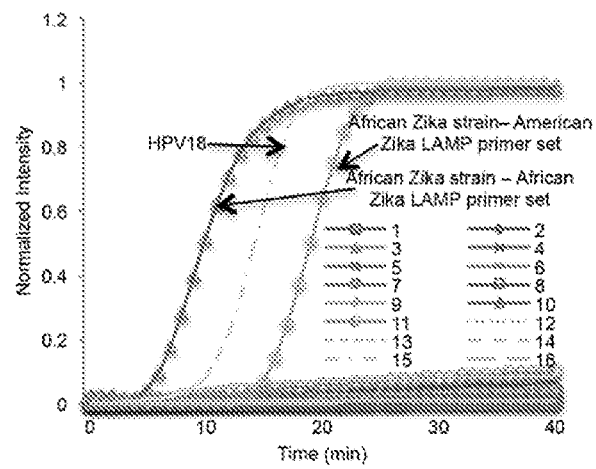
FIG. 12A  FIG. 12B
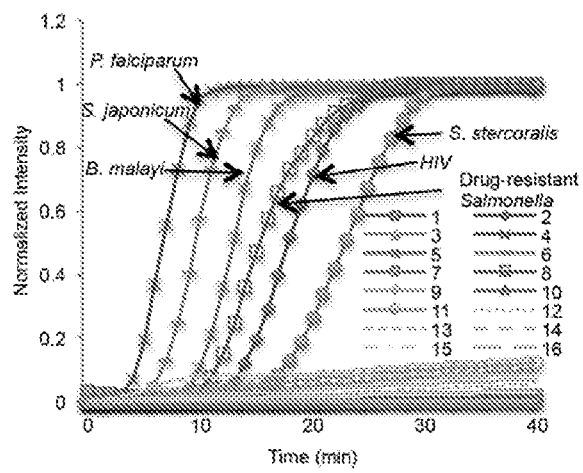
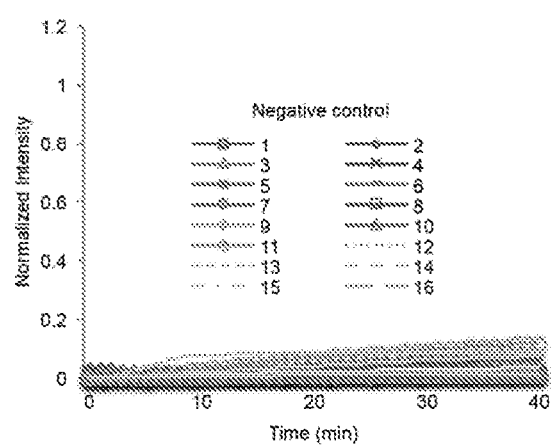
FIG. 12C  FIG. 12D
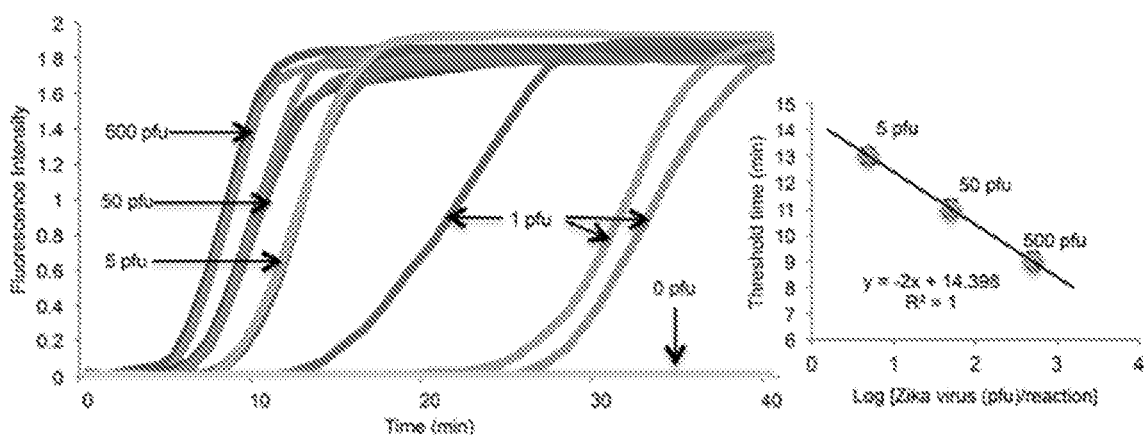
FIG. 12E  FIG. 12F

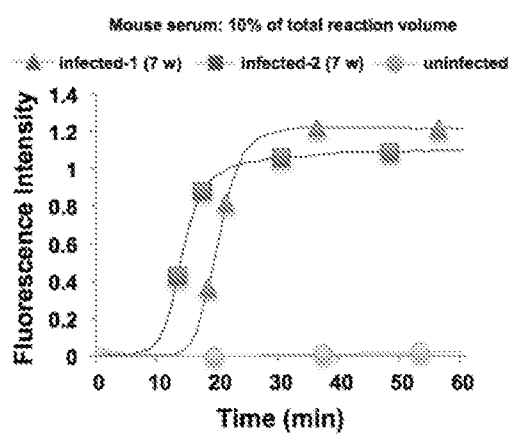
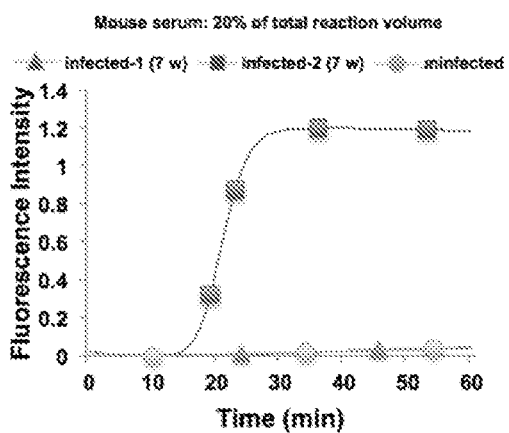
FIG. 14A FIG. 14B
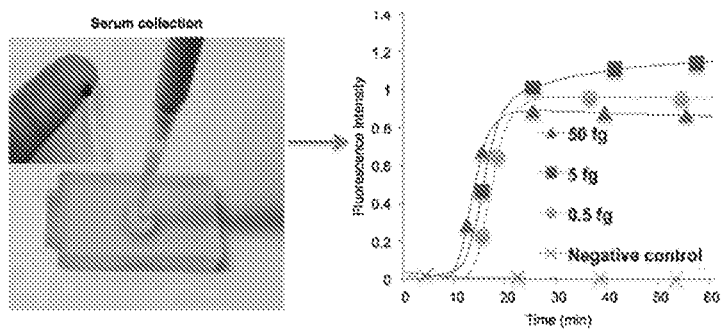
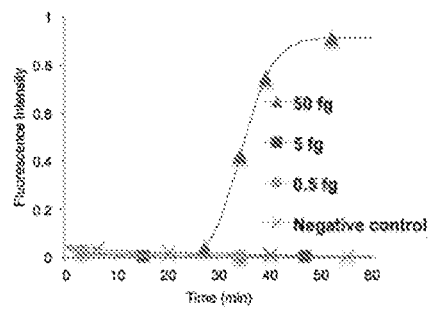
FIG. 14C FIG. 14D FIG. 14E

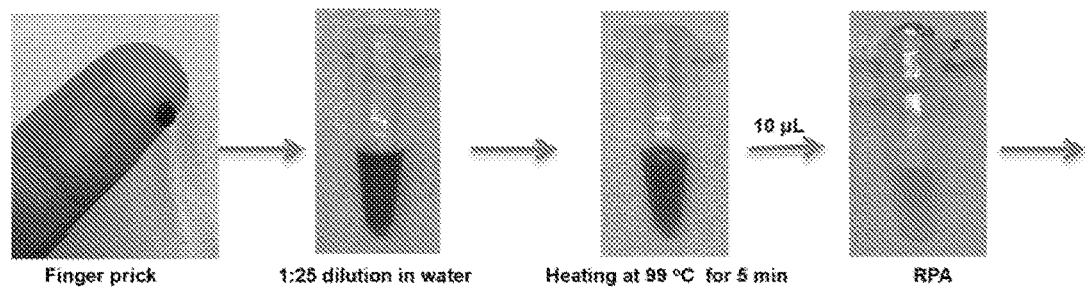
FIG. 15A
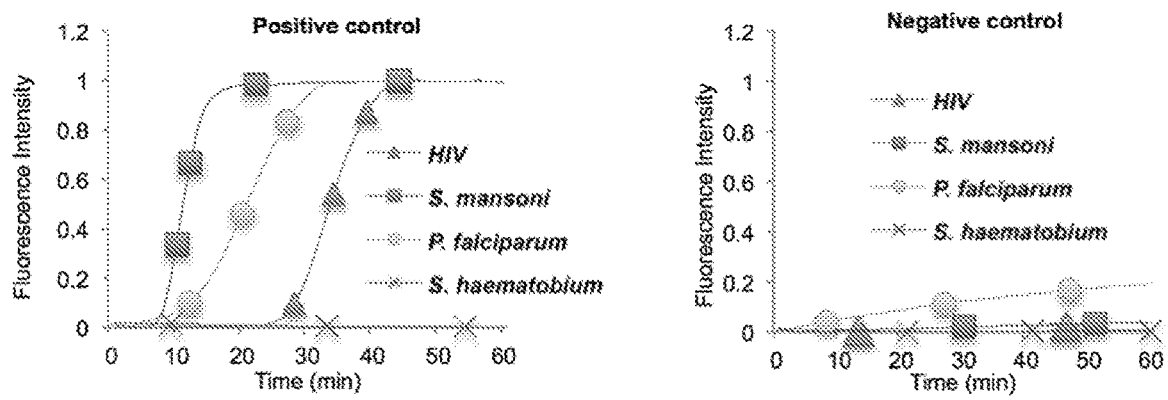
FIG. 15B
FIG. 15C

| Time for limit of detection (LOD) of various nested amplification methods. ||||| 
| Method | Target | Time for LOD |||
| | | 1st-stage | 2nd-stage | Total |
| RAMP[a] | Schistosoma mansoni | 00:20:00 | 00:11:00 | 00:31:00 |
| | Plasmodium falciparum | 00:20:00 | 00:06:00 | 00:26:00 |
| | Schistosoma haematobium | 00:20:00 | 00:14:00 | 00:34:00 |
| | HIV subtype B | 00:20:00 | 00:16:00 | 00:36:00 |
| Nested PCR[b] | Candida glabrata | 00:45:49 | 01:16:00 | 02:01:49 |
| isoPCR[b] | Candida glabrata | 00:45:49 | 00:14:42 | 01:00:32 |
| [a] Choose primer combination: F3, B3 (1st-stage)/F3, B3, FIP, BIP, Loop F, Loop B (2nd-stage) to compare. [b] Reference: M. J. Søe, M. Rohde, J. Mikkelsen, P. Warthoe, IsoPCR: An Analytically Sensitive, Nested, Multiplex Nucleic Acid Amplification Method. Clinical Chemistry 59, 436-439 (2013). |||||

FIG. 16

Cas9 guide RNA (cutting wildtype): CGAGGTTGATGGTGTTCAAATA –Tracer RNA sequence

Wildtype:

... ATAAACTTGTGGTAGTTGGAGCTGGTGGCGTAGGCAAGAGTGCCTTG ...  [PAM = TGG, arrow before TGG]

KRAS G12D:

... ATAAACTTGTGGTAGTTGGAGCTGATGGCGTAGGCAAGAGTGCCTTG ...  [No PAM]

FIG. 17A

TtAgo guide RNA (cutting wildtype): p-TCTACGCCACCAGCTCCAA

Wildtype: ... ATAAACTTGTGGTAGTTGGAGCTGGTGGCGTAGGCAAGAGTGCCTTG ...

KRAS G12D:

... ATAAACTTGTGGTAGTTGGAGCTGA*TGGCGTAGGCAAGAGTGCCTTG ...

FIG. 17B

Cas9 gRNA (Cutting ZIKV African Strain):

CGUCGUCGUUCUGGGGAGCC – Tracer RNA sequence

America zika RNA:

...AGGCAAAC<u>TGTCGTGGTTCTAGGGAGTC</u>|AAG|AAGGAGCAGTTCAC

[No PAM]

Africa zika RNA:

...AGGCAAAC<u>CGTCGTCGTTCTGGGGAGCC</u>|AGG|AAGGAGCCGTTCAC

[PAM]

FIG. 18A

TtAgo guid DNA (cutting ZIKV African Strain:

p-TCTCCTTCCTGGCTCCCCA

America zika RNA:

...CAAACTGTCGTGGTTC<u>TA*GGGAGTC*AAGAAGG*AG</u>CAGTTCACACG...

Africa zika RNA:

...CAAACTGTCGTGGTTC<u>TGGGGAGCC</u>AGGAAGGAGCAGTTCACACG...

FIG. 18B

MULTIPLE STAGE ISOTHERMAL ENZYMATIC AMPLIFICATION

CROSS-REFERENCE TO RELATED APPLICATIONS

This application is the National Stage Application of International Patent Application No. PCT/US2017/013403 filed Jan. 13, 2017, which claims priority to U.S. Provisional Application No. 62/278,095, filed Jan. 13, 2016, the disclosures of which are incorporated by reference in their entireties for any and all purposes.

GOVERNMENT RIGHTS

This invention was made with government support under grant number AI104418 awarded by the National Institutes of Health. The government has certain rights in the invention.

TECHNICAL FIELD

This disclosure relates to the field of nucleic acid amplification.

BACKGROUND

The detection and characterization of nucleic acids are standard molecular biology techniques often used in genetic studies, to diagnose disease, monitor food safety, detect environmental hazards and agents of bioterror, perform forensic analyses, and in a wide range of other applications. In many circumstances, the amount of template nucleic acid will be insufficient for direct detection and characterization and must first be amplified. Current protocols for amplifying limited amounts of nucleic acids employ more than one amplification step; generally at least one of the steps is a polymerase chain reaction (PCR), a time intensive methodology dependent on expensive thermocycler machinery. Due to the time and cost requirements of PCR, these current protocols are impractical for clinical or point-of-care settings. There exists a need for fast, highly selective methods of amplifying limited amounts of nucleic acids independent of expensive automated thermocycler machinery.

SUMMARY

In meeting this long felt need, the present disclosure provides methods for a multiple stage isothermal approach to amplifying nucleic acids. These methods are different from thermocycling protocols and are less expensive and much faster. These highly sensitive methods are also easily implemented in clinical, point-of-care, and other in-the-field settings to generate the necessary quantity of nucleic acids for downstream detection and characterization.

In one aspect, the present disclosure provides methods for multiple stage isothermal enzymatic amplification of nucleic acids, comprising: a first recombinase polymerase amplification reaction performed at a substantially isothermal temperature to generate a first amplification product, the nucleic acid serving as a template for the recombinase polymerase amplification reaction; and at least one subsequent loop-mediated isothermal amplification reaction performed at a substantially isothermal temperature to generate a second amplification product in an amount sufficient for recovery, testing, or characterization, the first amplification product serving as a template for the subsequent loop-mediated isothermal reaction.

Additional methods of multiple stage isothermal enzymatic amplification of a nucleic acid disclosed herein comprise a first substantially isothermal amplification reaction on the nucleic acid to generate a first amplification product, the nucleic acid serving as a template for the first substantially isothermal amplification reaction; and a second substantially isothermal amplification reaction on the first amplification product to generate at least one second amplification product in an amount sufficient for recovery, testing, or characterization, the first amplification product serving as a template for the second substantially isothermal amplification reaction.

BRIEF DESCRIPTION OF THE DRAWINGS

The summary, as well as the following detailed description, is further understood when read in conjunction with the appended drawings. For the purpose of illustrating the disclosed methods, there are shown in the drawings exemplary embodiments of the methods; however, the methods are not limited to the specific embodiments disclosed. In the drawings:

FIG. 5A illustrates the amplification of *P. falciparum* nucleic acid using a single RPA reaction. FIG. 5B shows detectable RPA amplification product for the highest concentration of template nucleic acid (3000 fg and 300 fg) whereas FIG. 5C shows multiple stage isothermal enzymatic amplification products for all starting template amounts. FIGS. 5D and 5E show enhanced sensitivity (to 30 fg) of template when an RPA reaction product is used as the template for a 20 minute or 50 minute loop-mediated isothermal amplification reaction.

FIG. 7A, FIG. 7B, FIG. 7C, FIG. 7D, FIG. 7E, and FIG. 7F depict the optimization of the multiple stage isothermal enzymatic amplification methodology. These figures illustrate multiple stage isothermal enzymatic amplification results using first stage amplification reaction products (RPA). FIGS. 7A, 7B, and 7C employed primer combinations 1, 2, and 3 that are identified in Table 2, respectively and 10 minute incubation times. FIG. 7D, FIG. 7E, and FIG. 7F employed primer combinations 1, 2, and 3 that are identified in Table 2, respectively and 20 minute incubation times.

FIGS. 8A-8D illustrate testing a sample for HIV, S. mansoni, P. falciparum, and S. haematobium, respectively, wherein only one nucleic acid template is present. FIG. 8E-FIG. 8H illustrate the detection of two different templates, and FIG. 8I illustrates the results of a negative control.

FIGS. 10A and 10D depict, respectively, the amplification curves of multiplexed multiple stage isothermal enzymatic amplification reaction and single-plex LAMP when the sample contains 3000, 300, 30, and 0 fg P. falciparum DNA. FIGS. 10B and 10E depict, respectively, the amplification curves of the multiple stage isothermal enzymatic amplification assay and single-plex LAMP when the sample contained 50, 5, 0.5, and 0 fg S. haematobium DNA. FIGS. 10C and 10F depict, respectively, amplification curves for the multiple stage isothermal enzymatic amplification assay and the single-plex LAMP when the sample contained 500, 100, 20, or 0 HIV-1 copies subtype B RNA.

FIG. 11A depicts the real time amplification curves for a multiplex RPA having a 50 minute incubation time. The agarose gel (2%) electrophoretogram of the purified amplification products of the multiplex RPA reaction (FIG. 11B) show spurious non-specific amplification products. FIG. 11C and FIG. 11D show the real time amplification curves for multiplexed multiple stage isothermal enzymatic amplification reactions with 20 and 50 minute incubation times FIG. 12A, FIG. 12B, FIG. 12C, and FIG. 12D illustrate amplification curves for 16-plex assay in the presence of specific nucleic acid templates. For these figures, the numbered lines in the legends represent the following: (1) S. mansoni, (2) HIV-1 clade B, (3) S. haematobium, (4) P. falciparum, (5) S. japonicum, (6) B. malayi, (7) S. stercoralis, (8) Drug-resistant Salmonella, (9) ZIKV-America strain (mex 2-81, Mexico), (10) ZIKV-Africa strain (MR 766, Uganda), (11) HPV-58, (12) HPV-52, (13) HPV-35, (14) HPV-45, (15) HPV-18, and (16) HPV-16. FIG. 12A depicts amplification curves for a sample containing HPV 16 and the American Zika strain. FIG. 12B illustrates amplification curves for a sample containing HPV-18, African zika strain (amplified with American zika LAMP primers), and African zika strain (amplified with African zika LAMP primers). FIG. 12C depicts amplification curves for a sample containing P. falciparum, S. japonicum, B. malayi, S. stecoralis, HIV, and drug-resistant Salmonella. FIG. 12D depicts amplification curves of a sample containing no template nucleic acid. FIG. 12E depicts the amplification curves obtained with the 16-plex multiple stage isothermal enzymatic amplification assay in the presence of 0, 1, 5, 50, and 500 PFU of the American ZIKV. FIG. 12F illustrates the threshold time ($T_{1/2}$, the time required for the signal to reach half its saturation value) as it relates to the amount of starting material.

FIG. 14A, FIG. 14B, FIG. 14C, FIG. 14D, and FIG. 14E illustrate the detection of amplification products of nucleic acids from serum samples. FIG. 14A and FIG. 14B depict real time amplification curves of multiple stage isothermal enzymatic amplification reactions, wherein 10% and 20% of the reaction volume was serum obtained from S. mansoni infected mice. FIG. 14C illustrates application of serum to a plasma separator and a human finger prick blood sample (inset). FIG. 14D and FIG. 14E illustrate real time amplification curves for multiple stage isothermal enzymatic amplification and a single loop mediated isothermal amplification reactions wherein the template is human serum spiked with S. mansoni.

FIG. 15A, FIG. 15B and FIG. 15C illustrate the detection of amplification products of nucleic acids obtained from whole blood. FIG. 15A provides a schematic protocol for processing whole blood samples to be used in an RPA reaction. FIG. 15B and FIG. 15C depict real time amplification curves for a multiple stage isothermal enzymatic amplification reaction using spiked human whole blood as a template and a multiple stage isothermal enzymatic amplification reaction with whole human blood containing no target nucleic acid.

FIG. 16 illustrates the time required to generate a detectable amount of an amplification product using the methods of the present invention, isoPCR, and nested PCR.

FIGS. 17A and 17B depict two options for removing unwanted wildtype KRAS nucleic acid. FIG. 17A illustrates the use of Cas9 to detect a mutation in the last two nucleotides (GG) of PAM site (NGG), where N stands for any nucleotide. FIG. 17B illustrates the use of TtAgo to remove non-mutated, or wildtype, nucleic acid. The arrows in FIGS. 17A and 17B indicate cut sites for the endonucleases. Asterisks indicate a change in the nucleotide sequence compared to the strand that has a recognizable cut site. The underlined sequence indicates the compliment of the RNA tracer sequencer.

FIG. 18A and FIG. 18B depict two options for differentiating the African and American strains of the Zika virus (ZIKV). FIG. 18A illustrates the use of Cas9 to differentiate America ZIKV strain from Africa ZIKV strain. FIG. 18B illustrates the use of TtAgo to differentiate America and Africa ZIKV strains. The arrows in FIGS. 17A and 17B indicate cut sites for the endonucleases. Asterisks indicate a change in the nucleotide sequence compared to the strand that has a recognizable cut site. The underlined sequence indicates the compliment of the RNA tracer sequencer.

DETAILED DESCRIPTION OF ILLUSTRATIVE EMBODIMENTS

Figure 1A:
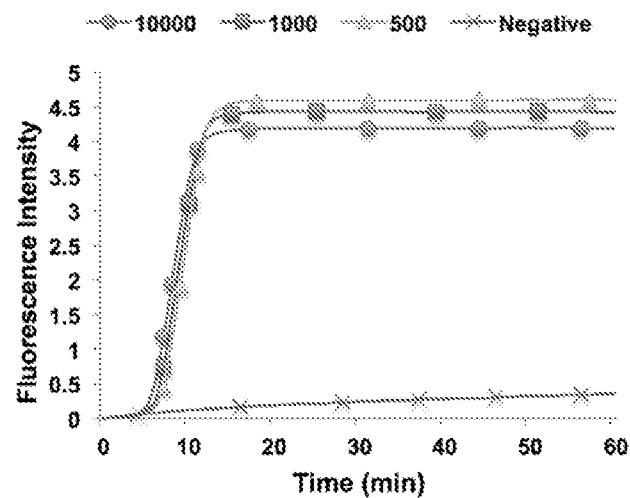
FIG. 1A illustrates the enhanced sensitivity of multiple stage isothermal enzymatic amplification of HIV clade C nucleic acid compared to a single loop-mediated isothermal amplification of HIV clade C nucleic acid as depicted in FIG. 1B.

The disclosed methods may be understood more readily by reference to the following detailed description taken in connection with the accompanying figures, which form a part of this disclosure. It is to be understood that the disclosed methods are not limited to the specific methods described and/or shown herein, and that the terminology used herein is for the purpose of describing particular embodiments by way of example only and is not intended to be limiting of the claimed methods.

Unless specifically stated otherwise, any description as to a possible mechanism or mode of action or reason for improvement is meant to be illustrative only, and the disclosed methods are not to be constrained by the correctness or incorrectness of any such suggested mechanism or mode of action or reason for improvement.

When a range of values is expressed, another embodiment includes from the one particular value and/or to the other particular value. Further, references to values stated in ranges include each and every value within that range. All ranges are inclusive and combinable. When values are expressed as approximations, by use of the antecedent "about," it will be understood that the particular value forms another embodiment. Reference to a particular numerical value includes at least that particular value, unless the context clearly dictates otherwise.

It is to be appreciated that certain features of the disclosed methods which are, for clarity, described herein in the context of separate embodiments, may also be provided in combination in a single embodiment. Conversely, various features of the disclosed methods that are, for brevity, described in the context of a single embodiment, may also be provided separately or in any subcombination.

As used herein, the singular forms "a," "an," and "the" include the plural.

Various terms relating to aspects of the description are used throughout the specification and claims. Such terms are to be given their ordinary meaning in the art unless otherwise indicated. Other specifically defined terms are to be construed in a manner consistent with the definitions provided herein.

The term "about" when used in reference to numerical ranges, cutoffs, or specific values is used to indicate that the recited values may vary by up to as much as 10% from the listed value. Thus, the term "about" is used to encompass variations of ±10% or less, variations of ±5% or less, variations of ±1% or less, variations of ±0.5% or less, or variations of ±0.1% or less from the specified value.

A "nucleic acid" can be a deoxyribonucleic acid (DNA) or ribonucleic acid (RNA) polymer. Nucleic acids can be single-stranded or double-stranded.

As used herein, polymerase chain reaction (PCR) refers to an enzymatic nucleic acid amplification process that involves multiple cycles of denaturing template nucleic acid, annealing primers, and synthesizing a nucleic acid strand complimentary to the template strand. Each cycle will involve raising and lowering the reaction temperature to provide the proper thermal environment for each step of the cycle. Denaturing template nucleic acid is usually accomplished using high temperature, while annealing primers requires a lower temperature. Synthesis of the nucleic acid complementary to the template strand will typically occur at a temperature between the temperatures used for denaturing and annealing.

Within the scope of the disclosed methods, "thermocycle" refers to an automated process of changing temperature at fixed time intervals during each cycle of an amplification reaction. Thermocycling is often used in PCR because the denaturing, annealing, and synthesizing steps typically are performed at different temperatures.

The term "substantially isothermal" describes reaction conditions that do not require thermocycling. A substantially isothermal reaction may have temperature changes at the beginning and end of an amplification reaction. For example, substantially isothermal reactions include reactions that employ a "hot start" mechanism, in which the reaction mixture is heated to a temperature necessary to activate a component of the reaction mixture and then optionally cooled to a temperature at which a nucleic acid polymerase catalyzes nucleic acid synthesis. Similarly, substantially isothermal reactions may employ a temperature to deactivate the amplification reaction, a temperature suitable for storage of the amplification products, a temperature for the release of stored reagents, or combination thereof. Thermocycling equipment can be employed to provide reaction conditions comprising a "hot start," the reaction temperature, a deactivating temperature, or a storage temperature. The temperature at which a polymerase catalyzes the formation of a nucleic acid strand can be substantially isothermal, especially if the enzyme is active or a range of temperatures at or near its ideal polymerization temperature.

As used herein, "template" refers to a nucleic acid, all or a portion of which is amplified during an amplification reaction. A template can be either single-stranded or double-stranded DNA or RNA. A template can also be a nucleic acid containing modified nitrogenous bases.

Disclosed herein are methods for the multiple stage isothermal amplification of nucleic acids, comprising: a first recombinase polymerase amplification reaction performed at a substantially isothermal temperature to generate a first amplification product, the nucleic acid serving as a template for the recombinase polymerase amplification reaction; and at least one subsequent loop-mediated isothermal amplification reaction performed at a substantially isothermal temperature to generate a second amplification product in an amount sufficient for recovery, testing, or characterization, the first amplification product serving as a template for the subsequent loop-mediated isothermal reaction.

Suitable recombinase polymerase amplification reactions include those described in Piepenburg et al., 4 PLoS Biol. 1115 (2006), employ a recombinase enzyme that coats single-stranded nucleic acids, which can then probe a template nucleic acid for sequence homology. When the template nucleic acid is double stranded, the coated single-stranded nucleic acids displace a strand of the template. Once a homologous sequence is identified, the single-stranded probe serves as a primer for synthesis of complementary nucleic acid, or amplification product. As no denaturation is necessary for this process, recombinase polymerase amplification reactions can be performed substantially isothermally.

The recombinase polymerase amplification reaction generates a first amplification product. "A first amplification product" is a population of nucleic acids produced during an amplification reaction. As used herein, "amplicon" refers to the nucleic acid sequence that will be amplified as well as the resulting nucleic acid polymer of an amplification reaction. The first amplification product is essentially a single amplicon in some embodiments. An essentially single amplicon can include the full length amplicon, prematurely terminated amplicons, amplicons containing sequence errors, or a combination thereof. In other embodiments, the first amplification product is a plurality of amplicons. If the desired amplification product is a single amplicon, the amplification reaction will be designed to amplify only the desired region. This is typically accomplished using primers that specifically promote amplification of only the desired region. Similarly, if a plurality of amplicons is desired, the amplification reaction will be designed to utilize multiple primer sets that specifically promote amplification of the desired regions.

The amplification product resulting from the first recombinase polymerase reaction is used in the disclosed methods as the initial template of a subsequent substantially isothermal loop-mediated isothermal amplification. Loop-mediated isothermal amplification reactions have been described previously. (Notomi et al., 28 Nucleic Acid Research e63 (2000)). Generally, loop-mediated isothermal amplification reactions employ multiple primers and a polymerase with high strand displacement characteristics. High strand displacement allows for amplification of template nucleic acids without temperature cycles to denature the nucleic acid, anneal primers, and elongate the newly synthesized nucleic acid strand.

The amplification reactions are performed substantially isothermally, preferably at a temperature that promotes optimal performance of a nucleic acid polymerase. In some embodiments of the claimed methods, at least one of the reactions will be performed at a temperature in the range of about 25° C. to about 65° C. In some aspects, the temperature range can be about 25° C. to about 63° C. In some aspects, the temperature range can be about 25° C. to about 61° C. In some aspects, the temperature range can be about 25° C. to about 59° C. In some aspects, the temperature range can be about 25° C. to about 57° C. In some aspects, the temperature range can be about 25° C. to about 55° C. In some aspects, the temperature range can be about 25° C. to about 53° C. In some aspects, the temperature range can be about 25° C. to about 51° C. In some aspects, the temperature range can be about 25° C. to about 49° C. In some aspects, the temperature range can be about 25° C. to about 47° C. In some aspects, the temperature range can be about 25° C. to about 45° C. In some aspects, the temperature range can be about 25° C. to about 43° C. In some aspects, the temperature range can be about 25° C. to about 41° C. In some aspects, the temperature range can be about 25° C. to about 39° C. In some aspects, the temperature range can be about 25° C. to about 37° C. In some aspects, the temperature range can be about 25° C. to about 35° C. In some aspects, the temperature range can be about 25° C. to about 33° C. In some aspects, the temperature range can be about 25° C. to about 31° C. In some aspects, the temperature range can be about 25° C. to about 29° C. In some aspects, the temperature range can be about 27° C. to about 65° C. In some aspects, the temperature range can be about 29° C. to about 65° C. In some aspects, the temperature range can be about 31° C. to about 65° C. In some aspects, the temperature range can be about 33° C. to about 65° C. In some aspects, the temperature range can be about 35° C. to about 65° C. In some aspects, the temperature range can be about 37° C. to about 65° C. In some aspects, the temperature range can be about 39° C. to about 65° C. In some aspects, the temperature range can be about 41° C. to about 65° C. In some aspects, the temperature range can be about 43° C. to about 65° C. In some aspects, the temperature range can be about 45° C. to about 65° C. In some aspects, the temperature range can be about 47° C. to about 65° C. In some aspects, the temperature range can be about 49° C. to about 65° C. In some aspects, the temperature range can be about 51° C. to about 65° C. In some aspects, the temperature range can be about 53° C. to about 65° C. In some aspects, the temperature range can be about 55° C. to about 65° C. In some aspects, the temperature range can be about 57° C. to about 65° C. In some aspects, the temperature range can be about 59° C. to about 65° C. In some aspects, the temperature range can be about 61° C. to about 65° C.

In some embodiments of the methods, at least one of the reactions is performed at a temperature in the range of about 55° C. to about 99° C. In some aspects, at least one of the reactions is performed at a temperature in the range of about 55° C. to about 80° C. In some aspects, at least one of the reactions is performed at a temperature in the range of about 55° C. to about 75° C. In some aspects, at least one of the reactions is performed at a temperature in the range of about 55° C. to about 70° C. In some aspects, at least one of the reactions is performed at a temperature in the range of about 55° C. to about 65° C. In some aspects, at least one of the reactions is performed at a temperature in the range of about 55° C. to about 60° C. In some aspects, at least one of the reactions is performed at a temperature in the range of about 60° C. to about 80° C. In some at least one of the reactions is performed at a temperature in the range of about 65° C. to about 80° C. In some aspects, at least one of the reactions is performed at a temperature in the range of about 70° C. to about 80° C. In some aspects, at least one of the reactions is performed at a temperature in the range of about 75° C. to about 80° C.

The loop-mediated isothermal amplification reaction will generate a second amplification product. This second amplification product will be a sufficient amount for downstream recovery, testing or characterization. "Recovery," as used in the present invention refers to any method that captures, isolates, obtains, or sequesters the amplification product. "Testing" refers to any method wherein the presence of the amplification product is confirmed or the amplification product is manipulated. "Characterization" refers to any process that elucidates a feature of the amplification product. Examples of characterizing an amplification product include, but are not limited to, determining the size of the amplification product, determining the sequence of the amplification product, and determining any sequence variation in the amplification product compared to the sequence of a reference sample.

In some aspects of the methods, the first amplification product serves as a template for a plurality of subsequent loop-mediated amplification reactions. A "plurality of subsequent loop-mediated amplification reactions" refers to more than one subsequent loop-mediated amplification reaction. The plurality of reactions can be employed to probe multiple targets or as redundant reactions to control for false-positive and false-negative results. A plurality of reactions can also be employed to generate a sufficient amount of a second amplification product for downstream recovery, testing or characterization.

In some embodiments, at least one of the amplification reactions employs a reverse transcriptase. A "reverse transcriptase" refers to an enzyme or enzymatic system that is capable of catalyzing the synthesis of DNA from an RNA template. Reverse transcription, the process of synthesizing DNA from a RNA template, can be accomplished isothermally.

The nucleic acid can be a region of an infectious agent or a genetic marker. "Infectious agent" refers to any species that is capable of entering and replicating within a host organism. Examples of infectious agents include, but are not limited to, bacteria, viruses, fungi, protozoa, algae, and helminths. Infectious agents may be parasitic, symbiotic, or may not have a deleterious or beneficial impact on the host organism.

In some aspects, the infectious agent is human immunodeficiency virus, *Schistosoma mansoni*, *Schistosoma haematobium*, *Plasmodium falciparum*, *Schistosoma japonicum*, *Brugia malayi*, *Strongyloides stercoralis*, drug-resistant *Salmonella*, ZIKV-America strain (mex 2-81, Mexico), ZIKV-Africa strain (MR 766, Uganda), HPV-58, HPV-52, HPV-35, HPV-45, HPV-18, HPV-16, or a combination thereof. In some aspects, the infectious agent is human immunodeficiency virus. In some aspects, the infectious agent is *Schistosoma mansoni*. In some aspects, the infectious agent is *Schistosoma haematobium*. In some aspects, the infectious agent is *Plasmodium falciparum*. In some aspects, the infectious agent is *Schistosoma japonicum*. In some aspects, the infectious agent is *Brugia malayi*. In some aspects, the infectious agent is *Strongyloides stercoralis*. In some aspects, the infectious agent is drug-resistant *Salmonella*. In some aspects, the infectious agent is ZIKV-America strain (mex 2-81, Mexico). In some aspects, the infectious agent is ZIKV-Africa strain (MR 766, Uganda). In some aspects, the infectious agent is HPV-58. In some aspects, the infectious agent is HPV-52. In some aspects, the infectious agent is HPV-35. In some aspects, the infectious agent is HPV-45. In some aspects, the infectious agent is HPV-18. In some aspects, the infectious agent is HPV-16.

Also provided are methods for amplifying a genetic marker. A "genetic marker" as used herein refers to any known nucleic acid sequence. Genetic markers are often associated with a biological condition, including but not limited to cancer, diabetes, and heart disease. Genetic markers are also used to track inherited traits, identify species, and compare genetic samples in forensic studies, along with a host of other uses. In some embodiments, the genetic marker is associated with foodborne pathogens, agents of bioterror, or environmental agents. "Foodborne pathogen" generally refers to microbes that cause foodborne illness. Foodborne pathogens can be bacteria, viruses, protozoa, algae, mold, worms, and any other parasite capable of infecting another organism, often after contact of contaminated food. Examples of food borne pathogens include, but are not limited to, *E. coli*, *Listeria monocytogenes*, and *Salmonella enterica*. The rapid and inexpensive method provided herein of amplifying the nucleic acid of foodborne pathogens can assist in the identification of the causative agent of foodborne illnesses and the tracking of the suspected tainted food.

"Agents of bioterror" refers to organisms, or toxins produced by those organisms, that can be purposefully employed to injure or kill. Examples of agents of bioterror include, but are not limited to, *Clostridium botulinum* and *Bacillus anthraces*. Both microbes produce powerful toxins, botulinum toxin and anthrax, respectively, that if dispersed can kill or injure unsuspecting victims. The disclosed methods allow for the rapid confirmation of an agent of bioterror.

Also provided here are methods for multiple stage amplification of nucleic acids comprising a first substantially isothermal amplification reaction to generate a first amplification product, the nucleic acid serving as a template for the first substantially isothermal amplification reaction; and a second substantially isothermal amplification reaction to generate at least one second amplification product in an amount sufficient for recovery, testing, or characterization, the first amplification product serving as a template for the second substantially isothermal amplification reaction.

In one embodiment, at least one reaction employs a reverse transcriptase. In another embodiment, each reaction employs an enzymatic system to amplify nucleic acids. "Enzymatic systems" include, but are not limited to polymerases, helicases, reverse transcriptases, and recombinases, and any combination thereof. In some aspects, each reaction is performed at a temperature optimized for the enzymatic system.

In some embodiments of the claimed methods, at least one of the reactions will be performed at a temperature in the range of about 25° C. to about 65° C. In some aspects, the temperature range can be about 25° C. to about 63° C. In some aspects, the temperature range can be about 25° C. to about 61° C. In some aspects, the temperature range can be about 25° C. to about 59° C. In some aspects, the temperature range can be about 25° C. to about 57° C. In some aspects, the temperature range can be about 25° C. to about 55° C. In some aspects, the temperature range can be about 25° C. to about 53° C. In some aspects, the temperature range can be about 25° C. to about 51° C. In some aspects, the temperature range can be about 25° C. to about 49° C. In some aspects, the temperature range can be about 25° C. to about 47° C. In some aspects, the temperature range can be about 25° C. to about 45° C. In some aspects, the temperature range can be about 25° C. to about 43° C. In some aspects, the temperature range can be about 25° C. to about 41° C. In some aspects, the temperature range can be about 25° C. to about 39° C. In some aspects, the temperature range can be about 25° C. to about 37° C. In some aspects, the temperature range can be about 25° C. to about 35° C. In some aspects, the temperature range can be about 25° C. to about 33° C. In some aspects, the temperature range can be about 25° C. to about 31° C. In some aspects, the temperature range can be about 25° C. to about 29° C. In some aspects, the temperature range can be about 27° C. to about 65° C. In some aspects, the temperature range can be about 29° C. to about 65° C. In some aspects, the temperature range can be about 31° C. to about 65° C. In some aspects, the temperature range can be about 33° C. to about 65° C. In some aspects, the temperature range can be about 35° C. to about 65° C. In some aspects, the temperature range can be about 37° C. to about 65° C. In some aspects, the temperature range can be about 39° C. to about 65° C. In some aspects, the temperature range can be about 41° C. to about 65° C. In some aspects, the temperature range can be about 43° C. to about 65° C. In some aspects, the temperature range can be about 45° C. to about 65° C. In some aspects, the temperature range can be about 47° C. to about 65° C. In some aspects, the temperature range can be about 49° C. to about 65° C. In some aspects, the temperature range can be about 51° C. to about 65° C. In some aspects, the temperature range can be about 53° C. to about 65° C. In some aspects, the temperature range can be about 55° C. to about 65° C. In some aspects, the temperature range can be about 57° C. to about 65° C. In some aspects, the temperature range can be about 59° C. to about 65° C. In some aspects, the temperature range can be about 61° C. to about 65° C.

In some embodiments of the claimed methods, at least one of the reactions will be performed at a temperature in the range of about 35° C. to about 45° C. In some aspects, the temperature range can be about 35° C. to about 43° C. In some aspects, the temperature range can be about 35° C. to about 41° C. In some aspects, the temperature range can be about 35° C. to about 39° C. In some aspects, the temperature range can be about 33° C. to about 45° C. In some aspects, the temperature range can be about 35° C. to about 45° C. In some aspects, the temperature range can be about 37° C. to about 45° C. In some aspects, the temperature range can be about 39° C. to about 45° C. In some aspects, the temperature range can be about 41° C. to about 45° C.

In some embodiments, at least one of the reactions is performed at a temperature in the range of about 55° C. to about 99° C. In some aspects, at least one of the reactions is performed at a temperature in the range of about 55° C. to about 80° C. In some aspects, at least one of the reactions is performed at a temperature in the range of about 55° C. to about 75° C. In some aspects, at least one of the reactions is performed at a temperature in the range of about 55° C. to about 70° C. In some aspects, at least one of the reactions is performed at a temperature in the range of about 55° C. to about 65° C. In some aspects, at least one of the reactions is performed at a temperature in the range of about 55° C. to about 60° C. In some aspects, at least one of the reactions is performed at a temperature in the range of about 60° C. to about 80° C. In some aspects, at least one of the reactions is performed at a temperature in the range of about 65° C. to about 80° C. In some aspects, at least one of the reactions is performed at a temperature in the range of about 70° C. to about 80° C. In some aspects, at least one of the reactions is performed at a temperature in the range of about 75° C. to about 80° C.

Suitable methods for a substantially isothermal first amplification reaction include, but are not limited to, recombinase polymerase amplification, loop-mediated isothermal amplification, nucleic acid sequence-based amplification, helicase dependent amplification, or multiple displacement amplification. In one aspect, at least one of the reactions is a recombinase polymerase amplification reaction. In another aspect, at least one of the reactions is a loop-mediated isothermal amplification. In another aspect, the first substantially isothermal amplification reaction is a recombinase polymerase reaction and the second substantially isothermal amplification reaction is a loop-mediated isothermal amplification reaction.

In another aspect, at least one of the amplification reactions is helicase dependent reaction. Helicase dependent amplification is a process for isothermally amplifying nucleic acids that utilizes a helicase enzyme or subunit thereof to denature the double stranded template nucleic acid. The single stranded DNA is then coated by single-stranded DNA binding proteins. Primers are able to then anneal to their target sequences on the template DNA strand, and a DNA polymerase then synthesizes the complementary strand. Helicase dependent reactions are described, for example, in Vincent et al., 5 EMBO Reports 795 (2004).

In some aspects, at least one of the amplification reactions is a nucleic acid sequence-based amplification reaction. Nucleic acid sequence-based amplification is a substantially isothermal nucleic acid amplification process that utilizes a reverse transcriptase, RNAseH, and an RNA polymerase. (Compton et al., 350 Nature 91 (1991)). Essentially, an RNA template is reverse transcribed to yield a complimentary DNA molecule. The RNA and DNA molecules anneal to form an RNA-DNA hybrid molecule, which is then treated with RNAseH to degrade the RNA molecule. Primers driven synthesis of a second strand of DNA yields a double-stranded DNA molecule. An RNA polymerase then generates an RNA molecule, and the amplification cycle can then be repeated.

In some aspects, at least one of the amplification reactions is a multiple displacement amplification reaction. Multiple displace amplification is a substantially isothermal nucleic acid amplification method that employs random hexamer primers and a strand displacing polymerase, as disclosed in Blanco et al., 264 J. Biol. Chem. 8935 (1989). Because the method uses random hexamers and does not selectively amplify targets, multiple displacement amplification is often used as a first amplification step when multiple amplification steps are required. Multiple displacement reactions can also be used for whole genome amplification.

The first amplification product can be a single amplicon or a plurality of amplicons. In some embodiments, the first amplification product is essentially a single amplicon. In other embodiments, the first amplification product is a plurality of amplicons. Because the first stage amplification product will be an amount insufficient for recovery, testing, or characterization, the first amplification product will serve as the template for the second stage amplification a single reaction or a plurality of reactions. In some embodiments, the first amplification product serves as a template for a plurality of second substantially isothermal amplification reactions. The second stage amplification reaction can be designed such that at least some of the second substantially isothermal amplification reactions generate a plurality of amplicons.

The second amplification product will be in an amount sufficient for recovery, testing, or characterization. The second amplification product can comprise essentially one amplicon, one or more amplicons, two to ten amplicons, or more than ten amplicons. In some embodiments, the second amplification product comprises one or more amplicons. In other embodiments, the second amplification product comprises essentially one amplicon. In other embodiments, the second amplification product comprises two to ten amplicons.

In other embodiments, the second amplification product comprises more than ten amplicons. In some embodiments, the second amplification product comprises 11, 12, 13, 14, 15, 20, 25, 30, or even 50 amplicons.

Preferred embodiments of the disclosed methods include a first stage amplification reaction, the product of this first stage amplification reaction serving as the template for a second amplification reaction. Additional embodiments comprise one or more additional isothermal amplification reactions. Additional substantially isothermal reactions can be any substantially isothermal reaction described above. The amplification product of the preceding stage will serve as the template for the additional substantially isothermal amplification reaction.

EXAMPLES

The following examples are provided to further describe some of the embodiments disclosed herein. The examples are intended to illustrate, not to limit, the disclosed embodiments. Unless otherwise disclosed, the primers used in the following amplification reactions (other than Example 1) are described in Table 1.

TABLE 1

LAMP Primer Sequences

| Target | Amplicon length | Primer | Primer Sequence (5'-3') |
|---|---|---|---|
| HIV subtype B[S1] | 225 bp | F3 | ATTATCAGAAGGAGCCACC |
| | | B3 | CATCCTATTTGTTCCTGAAGG |
| | | FIP | CAGCTTCCTCATTGATGGTTTCTTTTTAACACCATGCTAAACACAGT |
| | | BIP | TGTTGCACCAGGCCAGATAATTTTGTACTGGTAGTTCCTGCTATG |
| | | Loop F | TTTAACATTTGCATGGCTGCTTGAT |
| | | Loop B | GAGATCCAAGGGGAAGTGA |
| S. mansoni*,[S2] | 206 bp | F3 | TTATCGTCTATAGTACGGTAGG |
| | | B3 | ATACTTTAACCCCCACCAA |
| | | FIP | GCCAAGTAGAGACTACAAACATCTTTGGGTAAGGTAGAAAATGTTGT |
| | | BIP | AGAAGTGTTTAACTTGATGAAGGGGAAACAAAACCGAAACCACTA |
| | | Loop F | CTGCACGAAATACAGAAT |
| | | Loop B | GTATGTTCTGTCCTCTTG |
| P. falciparum[S3] | 220 bp | F3 | TCGCTTCTAACGGTGAAC |
| | | B3 | AATTGATAGTATCAGCTATCCATAG |
| | | FIP | GGTGGAACACATTGTTTCATTTGATCTCATTCCAATGGAACCTTG |
| | | BIP | GTTTGCTTCTAACATTCCACTTGCCCGTTTTGACCGGTCATT |
| | | Loop F | CACTATACCTTACCAATCTATTTGAACTTG |
| | | Loop B | TGGACGTAACCTCCAGGC |
| S. haematobium[S4] | 199 bp | F3 | CTTTCTAAGCCCGCGATA |
| | | B3 | GCGCATTACACTTGGTCT |
| | | FIP | TACCCCTAACTTCGTGGTCTCCCCCCCTTATTTTAGGGTGC |
| | | BIP | CTCCCTATATAACATGGCGAGTAAGACTATGAAATCAGTGTTTTCGG |
| | | Loop F | GGTGCGCTTTGTTTTCCGT |
| | | Loop B | ACCATGTGTAAAGCGCGTCAAA |
| B. malayi[S5] | 322 bp | F3 | GCGCATAAATTCATCAGC |
| | | B3 | GCAAAACTTAATTACAAAAGCG |
| | | FIP | GCTTTTTTTAGTAGTTTTGGCACTTCTTACATTAGACAAGGAAATTGG |
| | | BIP | GAAAYTAATTGACTATGTTACGTGCACAACACAATATACGACCAGC |
| | | Loop F | AATTARAATTAAAATTGATAAAT |
| | | Loop B | ATTGTACCAGT |
| S. stercoralis[S6] | 184 bp | F3 | GTGTAGGCTGGCGTAGT |
| | | B3 | TTTCAATTTTAGCTTAGGACC |
| | | FIP | GCTACTATCACCAAGATCTGCACGCATTGAAGGTTATAAGCGTAAG |
| | | BIP | ACACAAGTGAGAATCTTGTGGACCTAACTCACAGTCAAATGATGT |
| | | Loop B | CGAAGTGGAAAAGGGTTTCACG |
| S. japonicum[S7] | 301 bp | F3 | ACTTCTAGTGGTGTTCGTCAGGCTTGT |
| | | B3 | CTAACTTTGGTGCCGAATTAAGCCA |
| | | FIP | AGGGAAATCAGACGATGACAATGCTATCTCCATTTTTATTTAA |
| | | BIP | TTTGACCACCTTAAACATGAATGAAGTAACATTTTACATTTGGA |
| | | Loop F | TCTAAAAGTATGTCAATGATAA |
| | | Loop B | AAGCATGCTTGGGATGCGATTCTC |
| Drug-resistant Salmonella** | 211 bp | F3 | TGCAACCATTAAAACTGGCG |
| | | B3 | TGGAGCGTTTTCTCCTGAAC |
| | | FIP | TACGGGCTTCCCTTCGCGATAGTGGATTACGGTTCCGCAGA |
| | | BIP | GCCGAAGCCTATGGCGTGAAGTGGCTGGCATCCATGTT |
| | | Loop F | CCCAGGCATAATCTTTTTGTTCGT |
| | | Loop B | ATCCAGCGTTATTGATATGGCC |
| ZIKV-America strain (mex 2-81, Mexico)***,[S8] | 205 bp | F3 | AGTTCAAGGACGCACATGC |
| | | B3 | AACGCTGCGR****TACACAAG |
| | | FIP | GCCTCY****AGAGCTCCAGCAAG-AGGCAAACTGTCGTGGTTC |
| | | BIP | GTGCAAAGGGAAGGCTGTCCTC-GAGTATGACACGCCCTTCAA |
| | | Loop F | CTGCTCCTTCTTGACTCCCTA |
| | | Loop B | TGGCCACTTGAAATGTCGC |
| ZIKV-Africa strain (MR 766, Uganda)***,[S8] | 218 bp | F3 | GAAGGAGCCGTTCACACG |
| | | B3 | CCTGCATACTGCACCTCC |
| | | FIP | GGCGGCATTTCAAATGGCCAG-CTCGCTGGAGCTCTAGAGG |
| | | BIP | TATTCCTTGTGCACTGCGGCA-TGACTGTTCCATGCAGTGTT |
| | | Loop F | CCTTTGCACCATCCATCTCAG |
| | | Loop B | TTCACATTCACCAAGGTCCCA |
| HPV16[S9] | 301 bp | F3 | CAAATTATTTTCCTACACCTAGTGG |
| | | B3 | GTCATAACGTCTGCAGTTAAGG |
| | | FIP | GTGGCCCTGTGCTCGTTG-TCTATGGTTACCTCTGATGCC |
| | | BIP | CACGCAGTACAAATATGTCA-CCCCATGTCGTAGGTACTCC |
| | | Loop F | GCTGCCATATCTACTTCAGAAACTACA |

TABLE 1-continued

LAMP Primer Sequences

| Target | Amplicon length | Primer | Primer Sequence (5'-3') |
|---|---|---|---|
| HPV18[S9] | 309 bp | F3 | TGTATTCTCCCTCTCCAAGTG |
| | | B3 | GAATATAGGACATAACATCTGCAG |
| | | FIP | GCCAGCAAACACCATTGTTA-CTCTATTGTTACCTCTGACTCCC |
| | | BIP | ACCACTCGCAGTACCAATTTAAC-CCTCAACATGTCTGCTATACTGC |
| | | Loop F | ACCCTGTGCCTTATGTAACC |
| HPV35[S9] | 206 bp | F3 | CCTATAGGTGAACATTGGG |
| | | B3 | GGATATTTGCAAATGGAACTG |
| | | FIP | GTTTAGTAACTCCAAAGGAGGAC-AAAGGCACACCTTGTAATGC |
| | | BIP | GGGACATGGTAGACACAGGA-CATATATCTAGGGGAACATCAC |
| | | Loop F | CATTCTCCTGCTTTTACCTGGT |
| HPV45[S9] | 225 bp | F3 | GAAACACAACGTTTGGTTTGGGC |
| | | B3 | GTGCTCACCAATAGCAGGTAC |
| | | FIP | TAAAATGGATGGCCACTTAGGCC-GGTATGGAAATTGGTCGTGGGC |
| | | BIP | GGATGATACAGAAAGTGCTCA-AAATACACAGCTGTGTTTGC |
| | | Loop F | CAATACCTAAAGGCTGCC |
| HPV52[S9] | 323 bp | F3 | GCCACTGTACAAAGCAGTGC |
| | | B3 | TGAATGTATGTCATAACATCAGCTG |
| | | FIP | ATTATTGTGGCCCTGCGCACG-TTCTATGGTAACCTCAGAATCCC |
| | | BIP | ACCACTCGTAGCACTAACATGAC-TCGCCATGACGAAGGTATTCCT |
| | | Loop B | GCTGAGGTTAAAAAGGAAAGCACA |
| HPV58[S9] | 214 bp | F3 | GACGTGAGCAGATGTTTGT |
| | | B3 | CCATTGTTATGACCTTGTGC |
| | | FIP | GGATAACTGCAGTATTACCGGACC-TAGGGCTGGAAAACTTGG |
| | | BIP | TCCAACTCCTAGTGGCTCTATAG-CGCTGTAGCCAATAAGGC |
| | | Loop B | CCTCAGAATCACAATTATTTAATAAGCC |

*Loop F and Loop B are absent in the original LAMP primer set[S3], and were custom-designed to increase LAMP efficiency.
**The LAMP primer set was custom-designed to detect the blaCMY-2 beta-lactamase gene in *Salmonella* Newport, the most common *Salmonella enterica* serotype in the USA.
***The LAMP primer sets for ZIKV American and African strains are newly designed using the same strategy as described in reference S8.
****R and Y indicate mixtures of primers in equal proportions, where R = A, G and Y = C, T Example 1: Multiple Stage Isothermal Enzymatic Amplification of HIV RNA Clade C Conventional recombinase polymerase amplification (RPA) reaction was used for first stage amplification. First stage RPA reactions can be performed as singleplex reactions, which selectively amplify one amplicon or as multiplex reactions with multiple primer pairs, which selectively amplify multiple amplicons. HIV subtype C RNA with various virus copy numbers (10000, 1000, 500, 0) were used as templates. The F3 and B3 primers from the LAMP primer set were used as the RPA primers. A 50 µL RPA reaction was performed with the TwistAmp Basic RT kit (TwistDx, UK) that contained 480 nM of each of F3 and B3 primers, 1× rehydration buffer, and sample. To start the reaction 14 mM magnesium acetate was added to the reaction mix. The reactants were incubated at 37° C. for 20 min 1 µL aliquots of the product were used as template in one or more second stage isothermal amplification reactions, each with a single specific loop LAMP primer set (only BIP, FIP, Loop F, Loop B).

Second-stage reactions were performed with primers of 1.6 µM FIP and BIP, and 0.8 µM LF and LB, 1× Isothermal Mastermix (Optigene), 1 µL first stage RPA amplified product, and 1× EvaGreen dye (Biotium, Hayward, Calif.). Reactions were performed at 63° C. using the real-time detection system (Bio-Rad) operating at a fixed temperature for 60 min.

Figure 1B:
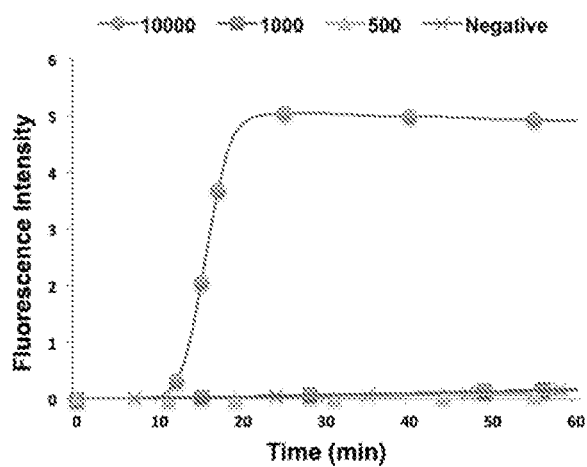

The multiple stage isothermal enzymatic amplification method is significantly more sensitive than single stage LAMP amplification. FIG. 1A shows that 500 copies of HIV subtype C RNA can be readily amplified and detected with multiple stage isothermal enzymatic amplification, while FIG. 1B shows that 10,000 copies of HIV subtype C RNA provided a detectable signal in one stage LAMP amplification.

Example 2: Multiple Stage Isothermal Enzymatic Amplification of HIV Clade B

Figure 2A:
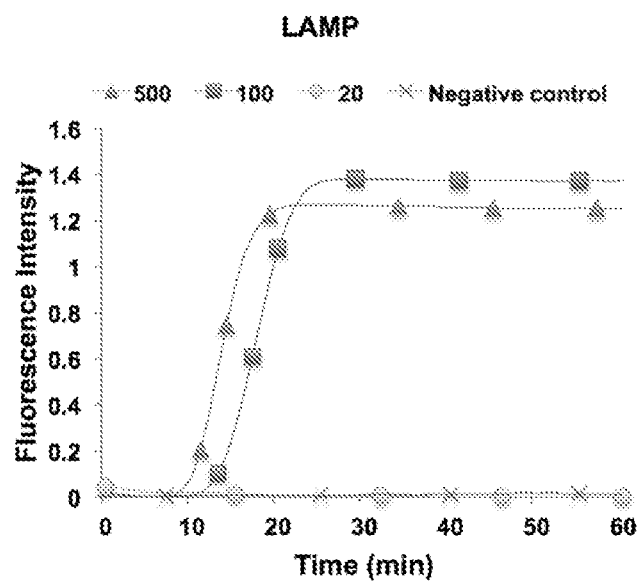
FIG. 2A and FIG. 2B illustrate the sensitivity of a single loop-mediated isothermal amplification (FIG. 2A) and of multiple stage isothermal enzymatic amplification (FIG. 2B) of HIV clade B nucleic acid.
Figure 2B:
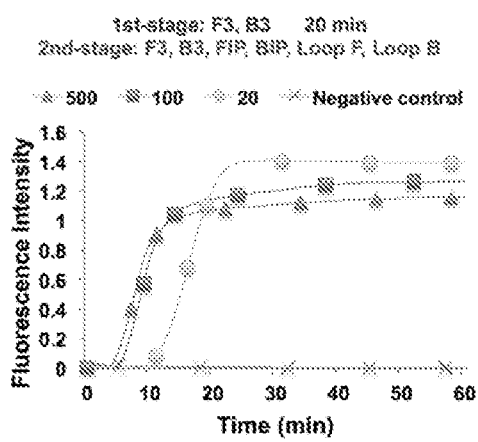

Real time amplification curves of samples containing 500, 100, 20, and 0 (negative control) copies of the HIV virus subtype B are shown in FIGS. 2A and 2B. FIG. 2A illustrates results obtained performing a single LAMP amplification with 6 LAMP primers (15 µl reaction volume). The LAMP process alone produced a detectable signal while amplifying a sample of 100 virus particles but no signal (false negative) was detected during the amplification of a sample of 20 virus particles. FIG. 2B illustrates the results of the multiple stage amplification process. The first stage consisted of RPA amplification with the LAMP primers F3 and B3 carried out in a reaction volume of 25 µl for 20 min. A small fraction (1 µl) of the first isothermal amplification reaction product was transferred to a second reaction chamber for a second isothermal LAMP amplification reaction with six LAMP primers (15 µl reaction volume). The combined multiple stage isothermal enzymatic amplification method produced a detectable amplification product from 20 virus copies and may be able to provide an even lower detection limit.

Figure 3A:
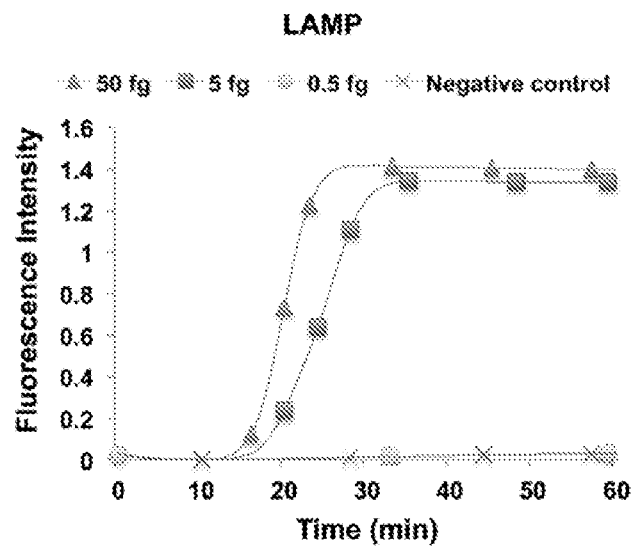
FIG. 3A and FIG. 3B illustrate the sensitivity of a single loop-mediated isothermal amplification (FIG. 3A) and of multiple stage isothermal enzymatic amplification of *Schistosoma mansoni* nucleic acid (FIG. 3B).
Figure 3B:
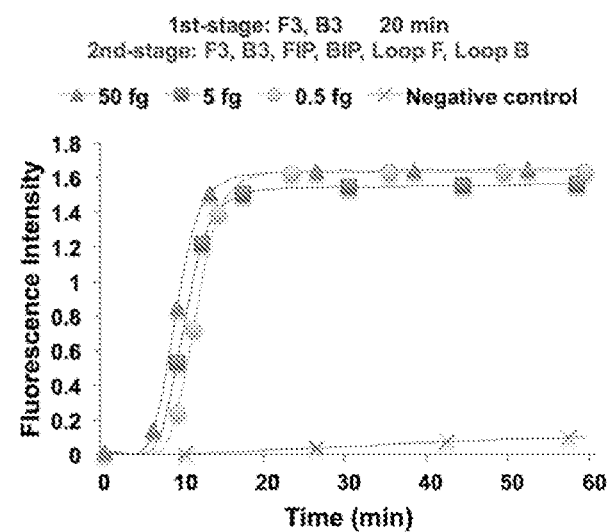

Example 3: Multiple Stage Isothermal Enzymatic Amplification of *Schistosoma mansoni* DNA Real time amplification curves of samples containing 50, 5, 0.5, and 0 fg (negative control) of *Schistosoma mansoni* DNA are shown in FIGS. 3A and 3B. FIG. 3A illustrates results obtained with LAMP amplification with 6 LAMP primers (15 µl reaction volume). The LAMP process alone produced a detectable signal while amplifying 5 fg of template molecules and no signal (false negative) was detected during the amplification of 0.5 fg of template molecules. FIG. 3B illustrates the results of the multiple stage amplification process. The first stage consisted of RPA amplification with the LAMP primers F3 and B3 carried out in a reaction volume of 25 µl for 20 min. A small fraction (1 µl) of the first isothermal amplification reaction product was transferred to a second reaction chamber for a second isothermal amplification reaction, specifically LAMP amplification with six LAMP primers (15 µl reaction volume). The combined multiple stage isothermal enzymatic amplification method produced a detectable amplification product from 0.5 fg of template molecules and may be able to provide an even lower detection limit.

Figure 4A:
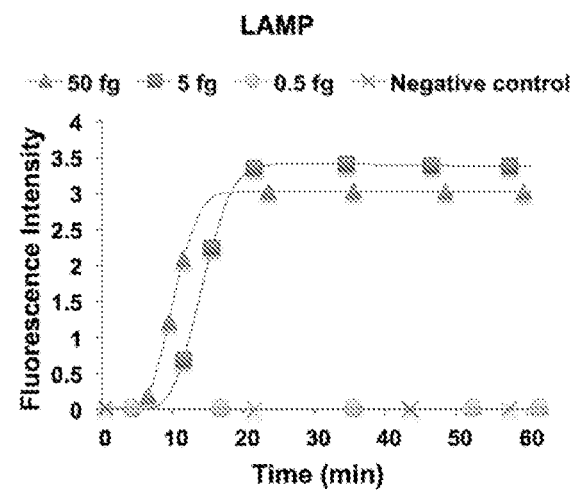
FIG. 4A and FIG. 4B illustrate the sensitivity of a single loop-mediated isothermal amplification (FIG. 4A) and of multiple stage isothermal enzymatic amplification (FIG. 4B) of *Schistosoma haematobium*.
Figure 4B:
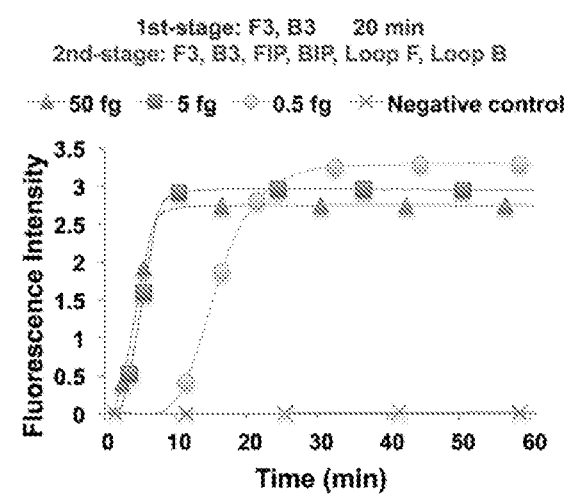

Example 4: Multiple Stage Isothermal Enzymatic Amplification of *Schistosoma haematobium* DNA Real time amplification curves of samples containing 50, 5, 0.5, and 0 (negative control) fg *Schistosoma haematobium* DNA are shown in FIGS. 4A and 4B. FIG. 4A illustrates results obtained with LAMP amplification alone with 6 LAMP primers (15 µl reaction volume). The LAMP process alone produced a detectable signal while amplifying 5 fg of template molecules and no signal (false negative) was detected while amplifying 0.5 fg of template molecules. FIG. 4B illustrates the results of the multiple stage amplification process. The first stage consisted of RPA amplification with the LAMP primers F3 and B3 carried out in a reaction volume of 25 µl for 20 min. A small fraction of the products of the first stage (1 µl) was transferred to a second reaction chamber for a second isothermal amplification reaction, specifically LAMP amplification with six LAMP primers (15 µl reaction volume). The combined multiple stage process produced a detectable amplification product from 0.5 fg of template molecules and may be able to provide an even lower detection limit.

Figure 5A:
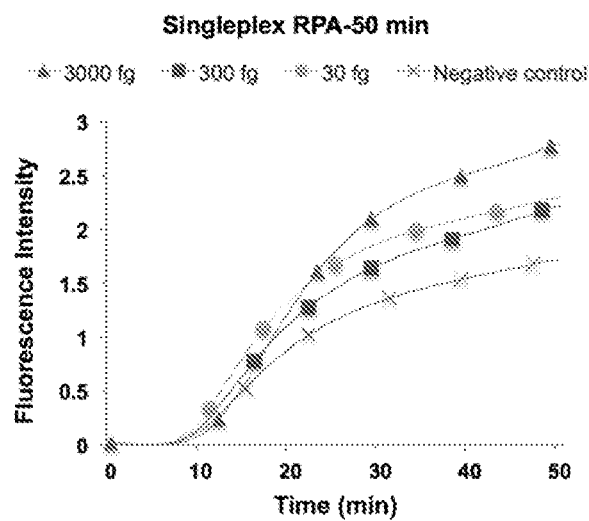
FIG. 5A, FIG. 5B, FIG. 5C, FIG. 5D, and FIG. 5E illustrate the sensitivities of a single Recombinase Polymerase Amplification (RPA) and of multiple stage isothermal enzymatic amplifications of *Plasmodium falciparum* nucleic acid.
Figure 5B:
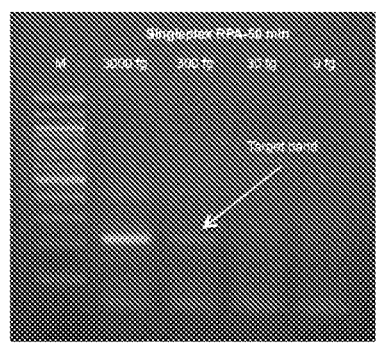
Figure 5C:
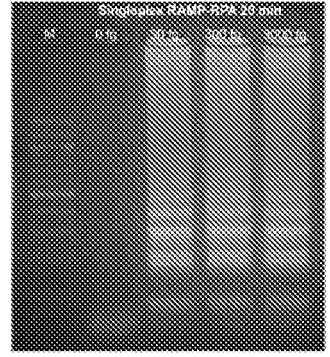
Figure 5D:
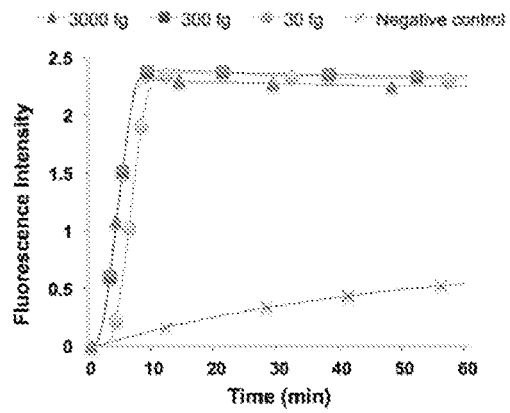
Figure 5E:
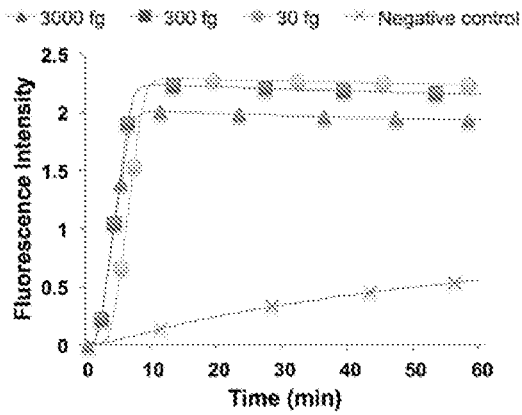

Example 5: Multiple Stage Isothermal Enzymatic Amplification of *Plasmodium falciparum* DNA Real time amplification curves of samples containing 3000, 300, 30, and 0 (negative control) fg *Plasmodium falciparum* DNA are shown in FIGS. 5A, 5B, 5E, and 5F. FIG. 5A illustrates results obtained with LAMP amplification alone with 6 LAMP primers (15 µl reaction volume). The LAMP process alone produced a detectable signal while amplifying 300 fg of template molecules and no signal (false negative) was detected while amplifying 30 fg of template molecules. FIG. 5B depicts the real time curves of a single-plex RPA amplification of *P. falciparum*. This assay contained the F3-B3 primer pair for *P. falciparum* (see Table 1) and was carried out for 50 minutes. There was non-specific amplification in RPA amplification as shown in the fluorescence intensity measured for the negative control, but this non-specific amplification can be resolved with subsequent specific, LAMP amplification. FIG. 5C is an agarose gel (2%) electrophoretogram for the single stage RPA amplification. Only relatively large template amounts (i.e., 3000 fg, and to a lesser extent 300 fg) were sufficient to observe an amplification product. FIG. 5D is an agarose gel (2%) electrophoretogram of the single plex RPA reaction carried out for 20 minutes. The blurred lanes indicate nonspecific amplification during the RPA reaction, which was expected. FIGS. 5E and 5F illustrate the results of the multiple stage amplification process. The first stage consisted of RPA amplification with the LAMP primers F3 and B3 carried out in a reaction volume of 25 µl for 20 min (FIG. 5E) or 50 min (FIG. 5F). A small fraction of the products of the first stage (1 µl) was transferred to a second reaction chamber for a second stage of the multiple stage process that consisted of LAMP amplification with six LAMP primers (15 µl reaction volume). The combined multiple stage process produced a detectable amplification product from 30 fg of template molecules and may be able to provide an even lower detection limit.

Figure 6A:
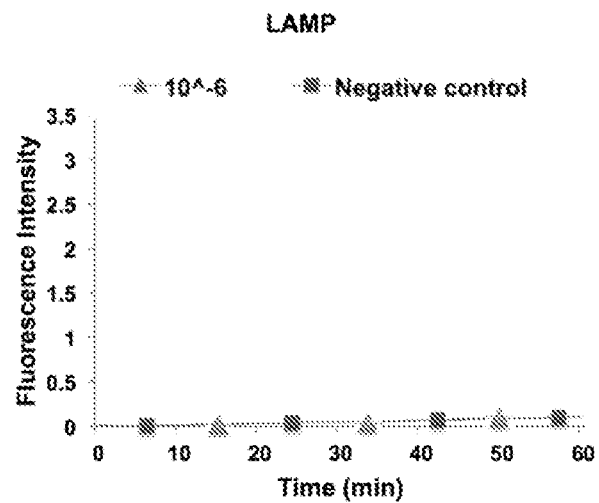
FIG. 6A and FIG. 6B illustrate the sensitivity of a single loop-mediated isothermal amplification (FIG. 6A) and of multiple stage isothermal enzymatic amplification (FIG. 6B) of $10^{-6}$ g of *Salmonella* nucleic acid.
Figure 6B:
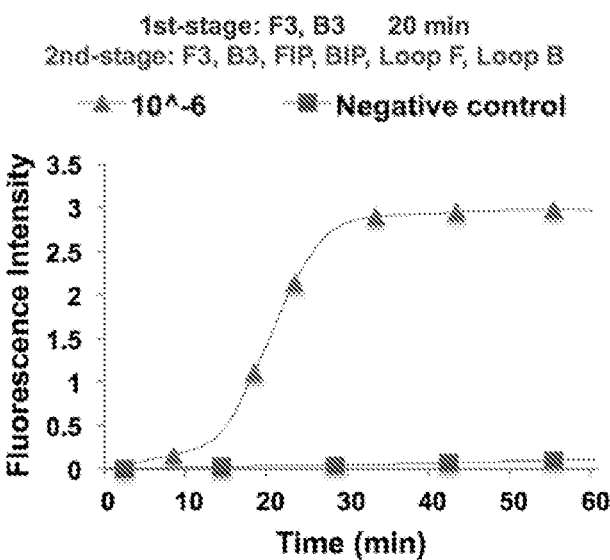

Example 6: Multiple Stage Isothermal Enzymatic Amplification of *Salmonella* DNA Real time amplification curves of samples containing 6 log ($10^6$ fold) diluted *Salmonella* DNA with unknown concentration and negative control are shown in FIGS. 6A and 6B. FIG. 6A illustrates results obtained with LAMP amplification alone with 6 LAMP primers (15 µl reaction volume). The LAMP method alone produced no signal (false negative) while amplifying the 6 log diluted original *salmonella* DNA sample. FIG. 6B illustrates the results of the multiple stage isothermal nucleic acid amplification. The first stage consisted of RPA amplification with the F3 and B3 LAMP primers carried out with a reaction volume of 25 µl for 20 min. A small fraction of the products of the first stage (1 µl) was transferred to a second reaction chamber for a second stage of the multiple stage isothermal nucleic acid amplification that consisted of LAMP amplification with six LAMP primers (15 µl reaction volume). The combined multiple stage isothermal amplification reaction produced a detectable amplification product from 6 log diluted template sample and may be able to provide an even lower detection limit.

Example 7: Optimization of First-Stage RPA Time and Primer Composition

FIGS. 7A-7F depict the superposed second-stage LAMP amplification curves with various concentrations of *S. mansoni* DNA. The first and second rows correspond, respectively, to 10 and 20 min first-stage (RPA) times. The first, second, and third columns correspond, respectively, to primer combinations 1, 2, and 3 (See Table 2).

TABLE 2

Comparison of Different First-Stage Reaction Times and Primer Combinations (N = 3).

| Primer combination | 1st-stage (RPA) | 2nd-stage (LAMP) | LOD* | 1$^{st}$ stage (min) | 2$^{nd}$ stage T½ ± s.d (min) | Total RAMP Time (min) |
|---|---|---|---|---|---|---|
| 1 | F3, B3 | FIP, BIP, Loop F, Loop B | 5 fg | 10.0 | 22 ± 5.0 | 32 ± 5.0 |
| 2 | F3, B3 | F3, B3, FIP, BIP, Loop F, Loop B | 5 fg | 10.0 | 19 ± 3.0 | 29 ± 3.0 |
| 3 | FIP, BIP | FIP, BIP, Loop F, Loop B | 50 fg | 10.0 | 15 ± 4.6 | 25 ± 4.6 |
| 1 | F3, B3 | FIP, BIP, Loop F, Loop B | 0.5 fg | 20.0 | 13.0 ± 0.6 | 33.0 ± 0.6 |
| 2 | F3, B3 | F3, B3, FIP, BIP, Loop F, Loop B | 0.5 fg | 20.0 | 11.0 ± 1.0 | 31.0 ± 1.0 |
| 3 | FIP, BIP | FIP, BIP, Loop F, Loop B | 50 fg | 20.0 | 13.0 ± 2.6 | 33.0 ± 2.6 |

*LOD values are the lowest target amount per reaction that was positively detected in 3 of 3 replicates.

When the RPA reaction time was 10 min and the sample contained 0.5 fg S. mansoni DNA, multiple isothermal enzymatic amplification failed to produce a detectable signal with any of the three primer combinations identified in Table 2 (FIG. 7A-7C). In contrast, when the RPA reaction time was 20 min and the same amounts of target DNA, multiple stage isothermal enzymatic amplification successfully produced detectable signals with primer combinations 1 and 2, but not with primer combination 3 (FIGS. 7D, 7E, and 7F, respectively). The negative controls for amplification reactions using primer combination 3 resulted in detectable reaction product. Thus, 20 min of first-stage RPA was sufficient to produce detectable signal in the presence of low abundance (0.5 fg) S. mansoni DNA.

Both stage one and stage two of the multiple stage isothermal enzymatic amplification, operating with primer combination 2, utilize the F3 and B3 primer pair. This reaction was also free of non-specific products (i.e., false positives).

Multiple stage isothermal enzymatic amplification with primer combination 3 uses the primer pair FIP and BIP in stage one and primers FIP, BIP, Loop F, and Loop B in stage two. Multiple stage isothermal enzymatic amplification with this particular primer combination lacks specificity and yields false positives. Without being bound by theory, the false positives may result from primer-dimers of FIP and BIP.

Example 8: Four-Plex Multiple Stage Isothermal Enzymatic Amplification

To demonstrate multiplexing with multiple stage isothermal enzymatic amplification, an assay was created to detect HIV-1 clade B, P. falciparum, and the schistosomes, S. haematobium and S. mansoni, in a single test. HIV is an RNA target, and the other three targets are DNA segments. This particular assortment of targets was selected because they are often co-endemic in developing countries (Fernandez-Soto, P. et al. A Loop-Mediated Isothermal Amplification (LAMP) Assay for Early Detection of Schistosoma mansoni in Stool Samples: A Diagnostic Approach in a Murine Model. Plos Neglected Tropical Diseases 8 (2014); Polley, S. D. et al. Mitochondrial DNA Targets Increase Sensitivity of Malaria Detection Using Loop-Mediated Isothermal Amplification. Journal of Clinical Microbiology 48, 2866-2871 (2010); Gandasegui, J. et al. The Rapid-Heat LAMPellet Method: A Potential Diagnostic Method for Human Urogenital Schistosomiasis. Plos Neglected Tropical Diseases 9 (2015); and Poole, C. B., Tanner, N. A., Zhang, Y. H., Evans, T. C. & Carlow, C. K. S. Diagnosis of Brugian Filariasis by Loop-Mediated Isothermal Amplification. Plos Neglected Tropical Diseases 6 (2012)).

The first assay was carried out on the benchtop with manual pipetting. The reaction time for the first-stage of multiple stage isothermal enzymatic amplification (with reverse transcriptase enzyme) was 20 min, and the reaction used a mixture of four pairs of F3-B3 primers, each pair specific to one of the targets. Thus, stage one could amplify any of the four targets, if present. The first-stage amplicons were then pipetted into four reaction chambers, each containing a primer set (FIP, BIP, Loop F, and Loop B) specific to one of the targets. The primers sequences are disclosed in Table 1.

Figure 8A:
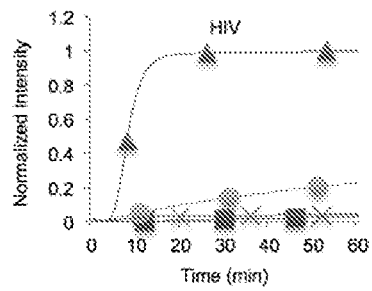
FIG. 8A, FIG. 8B, FIG. 8C, FIG. 8D, FIG. 8E, FIG. 8F, FIG. 8G, FIG. 8H, and FIG. 8I illustrate the design and testing of a multiplex multiple stage isothermal enzymatic amplification reaction.
Figure 8B:
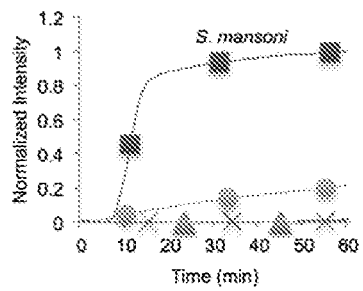
Figure 8C:
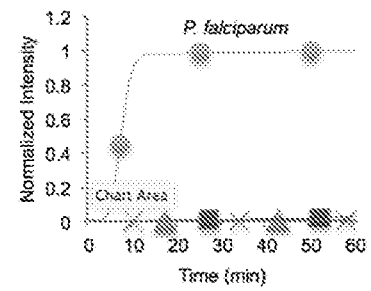
Figure 8D:
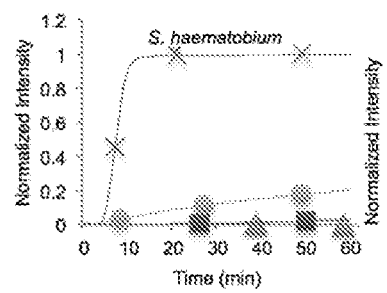

When only HIV RNA (20 copies) was present in the sample, only the LAMP tube with HIV-specific primers (triangle curve in FIG. 8A) produced a positive signal. As expected, the S. mansoni (square), P. falciparum (circle), and S. haematobium (X) tubes produced no signal above background. Similarly, only the S. mansoni, and S. haematobium tubes produced a signal when the sample contained, respectively, a S. mansoni, P. falciparum, and S. haematobium template (FIGS. 8B, 8C, and 8D, respectively).

Figure 8E:
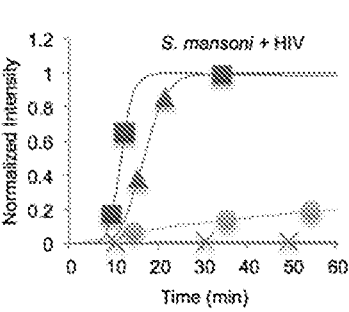
Figure 8F:
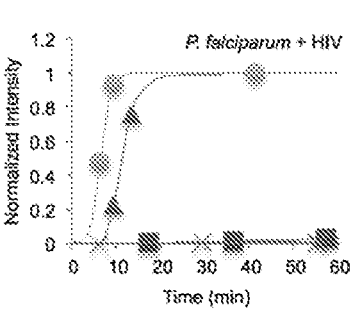
Figure 8G:
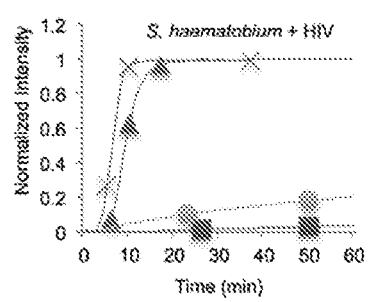
Figure 8H:
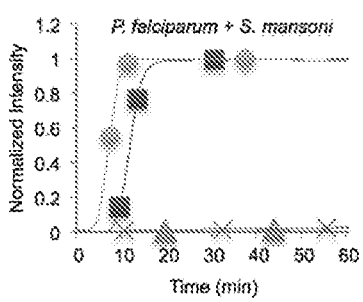
Figure 8I:
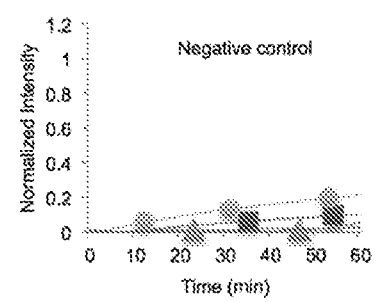

Next, samples containing the binary targets were analyzed: HIV RNA (20 copies) and S. mansoni DNA (0.5 fg) (FIG. 8E); HIV RNA (20 copies) and P. falciparum DNA (30 fg) (FIG. 9F); HIV RNA (20 copies) and S. haematobium DNA (0.5 fg) (FIG. 8G); and P. falciparum DNA (30 fg) and S. mansoni DNA (0.5 fg) (FIG. 8H); and a sample without any targets (no-target control) (FIG. 8 I). The amplification curves of the various specific LAMP reactors are superposed. For example, when the sample contained both HIV and S. mansoni, the HIV and S. mansoni tubes emitted fluorescence, while the P. falciparum, S. haematobium, and negative control tubes remained dark, indicating the absence of P. falciparum and S. haematobium targets. Similar performance was attained with other target combinations.

Figure 9:
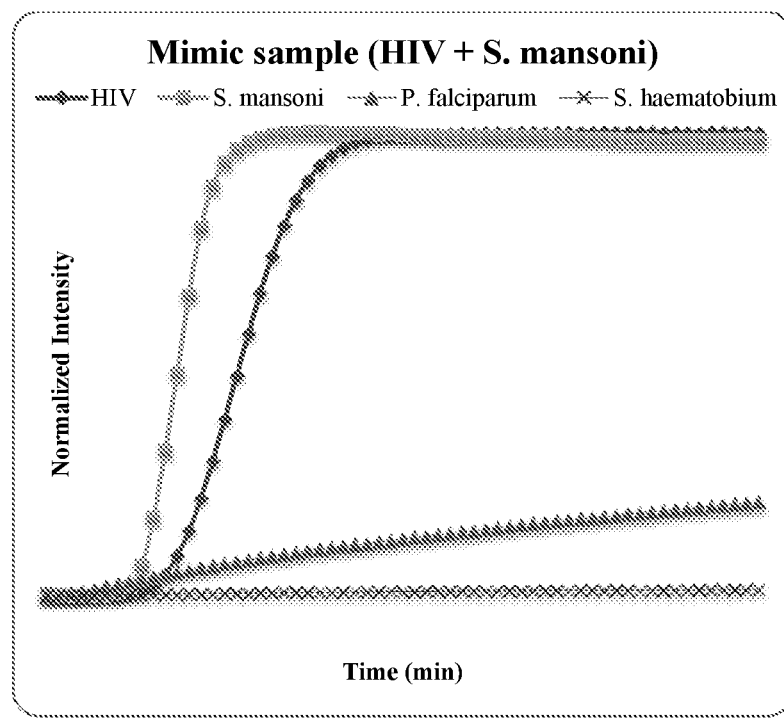
FIG. 9 illustrates the sensitivity, selectivity, and speed of the multiple stage enzymatic amplification of a sample containing more than one template.

Example 9: Multiple Stage Isothermal Enzymatic Amplification of HIV and Schistosoma mansoni DNA For this experiment, 25 µL RPA reaction was performed with the TwistAmp Basic kit (TwistDx, UK) containing 200 nM F3 or B3 primers for each target (HIV, *Schistosoma mansoni*, *Plasmodium falciparum*, *Schistosoma haematobium*), 1× rehydration buffer, 100 copies of HIV RNA, and 0.5 fg *Schistosoma mansoni*. To start the reaction, 14 mM magnesium acetate was added. The reactions were incubated at 37° C. for 20 min. 1 µL aliquots of the first stage amplification product were used as template for second stage isothermal amplification/detection reactions, each with a single specific LAMP primer set for HIV, *Schistosoma mansoni*, *P. falciparum*, and *Schistosoma haematobium*. Second stage reactions were performed with primers of 1.6 µM FIP and BIP, and 0.8 µM LF and LB, 0.2 µM F3 and B3, 1× Isothermal Mastermix (Optigene), 1 µL first-step PCR amplified product. Reactions were performed at 63° C. using a real-time detection system (Bio-Rad) operating at a fixed temperature for 60 min. FIG. 9 illustrates the sensitivity, selectivity, and speed of the present invention. Only the HIV and *Schistosoma mansoni* were detected in less than twenty minutes during the second isothermal enzymatic amplification reaction. There were no false positive or false negative results.

Figure 10A:
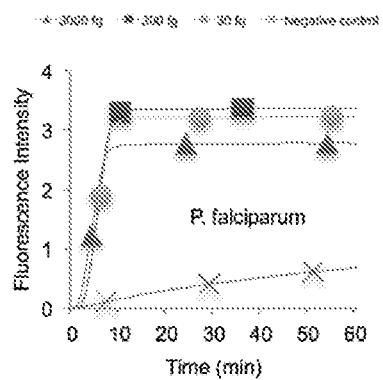
FIG. 10A, FIG. 10B, FIG. 10C, FIG. 10D, FIG. 10E, and FIG. 10F compare the performance of the multiplexed multiple stage isothermal enzymatic amplification (FIGS. 10A-10C) with that of LAMP alone (FIG. 10D-10F), in the presence of a single species of target in the sample.

Example 10: Comparison of the Sensitivity of Multiplexed RAM Multiple Stage Isothermal Enzymatic Amplification P with Single-Plex LAMP FIGS. 10A-10F compare the performance of the multiplexed multiple stage isothermal enzymatic amplification (FIGS. 10A-10C) with that of LAMP alone (FIGS. 10D-10F), in the presence of a single target in the sample. FIGS. 10A and 10D depict, respectively, the amplification curves of multiplexed multiple stage isothermal enzymatic amplification and single-plex LAMP when the sample contains 3000, 300, 30, and 0 fg *P. falciparum* DNA. The multiple stage isothermal enzymatic amplification assay successfully detects 30 fg of *P. falciparum* DNA, while the sensitivity of the LAMP assay alone was approximately tenfold lower (LOD=300 fg).

Figure 10B:
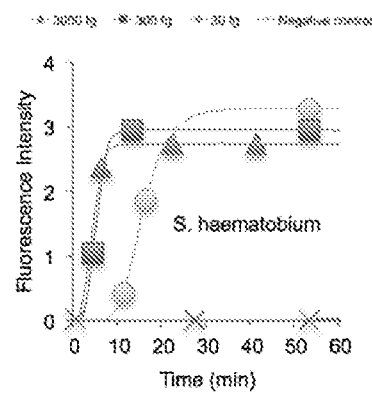
Figure 10C:
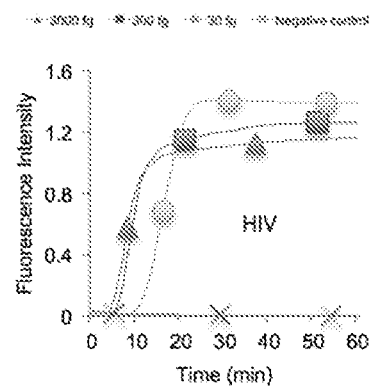
Figure 10D:
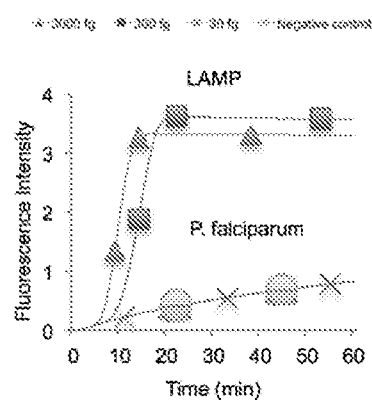
Figure 10E:
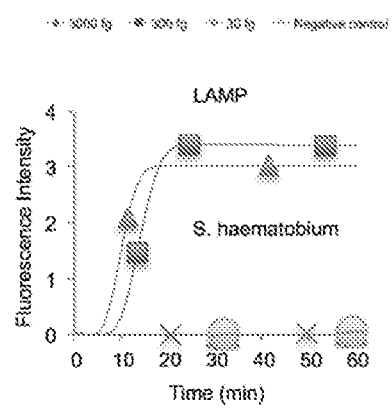

FIGS. 10B and 10E depict, respectively, the amplification curves of the multiple stage isothermal enzymatic amplification assay and single-plex LAMP when the sample contained 50, 5, 0.5, and 0 fg *S. haematobium* DNA. The multiple stage isothermal enzymatic amplification assay readily detected 0.5 fg *S. haematobium* DNA, while the sensitivity of the LAMP assay was again tenfold lower, with a limit of detection of 5 fg *S. haematobium* DNA.

Figure 10F:
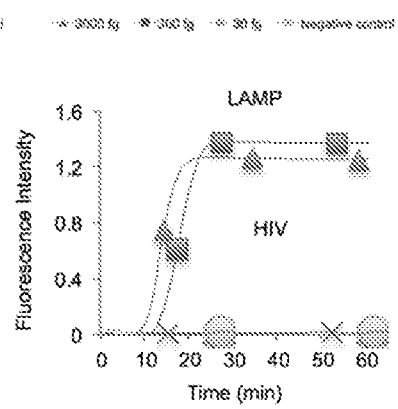

FIGS. 10C and 10F depict, respectively, amplification curves for the multiple stage isothermal enzymatic amplification assay and the single-plex LAMP when the sample contained 500, 100, 20, or 0 HIV-1 copies subtype B RNA. The multiple stage isothermal enzymatic amplification assay readily detected 20 copies HIV RNA while the sensitivity limit of the LAMP assay alone was approximately 100 copies.

To test reproducibility, each experiment was repeated in triplicate, and the $T_{1/2}$±s.d. values of the multiplexed multiple stage isothermal enzymatic amplification and single-plex LAMP assays are summarized in Table 3. The data indicated that multiplexed multiple stage isothermal enzymatic amplification had a good reproducibility. In addition, Table 3 illustrates that multiplexed multiple stage isothermal enzymatic amplification had a 5 to 10-fold better sensitivity than single-plex LAMP. Despite the introduction of multiple primer pairs in the first stage of the multiple stage isothermal enzymatic amplification, no nonspecific products (false positives) were evident.

TABLE 3

$T_{1/2}$ ± s.d. Values of the Multiplexed Multiple Stage Isothermal Enzymatic Amplification and Single-Plex LAMP

| | Target | Quantity ($T_{1/2}$ ± s.d.) | Quantity ($T_{1/2}$ ± s.d.) | Quantity ($T_{1/2}$ ± s.d.) |
|---|---|---|---|---|
| RAMP | *P. falciparum* | 3000 fg (5.8 ± 0.5) | 300 fg (6.0 ± 0.7) | 30 fg (8.0 ± 1.5) |
| | *S. haematobium* | 50 fg (5.0 ± 0.5) | 5 fg (6.0 ± 1.0) | 0.5 fg (14.0 ± 2.5) |
| | HIV subtype B | 500 copies (7.5 ± 1.0) | 100 copies (10.3 ±0.8) | 20 copies (16 ± 4.0) |
| LAMP | *P. falciparum* | 3000 fg (10.0 ± 1.0) | 300 fg (14.0 ± 2.5) | 30 fg (NS) |
| | *S. haematobium* | 50 fg (10.0 ± 0.5) | 5 fg (14.0 ± 3.5) | 0.5 fg (NS) |
| | HIV subtype B | 500 copies (14.0 ± 2.0) | 100 copies (18.0 ± 4.5) | 20 copies (NS) |

* Quantity indicates the number of copies or mass of nucleic acids per reaction.

Figure 11A:
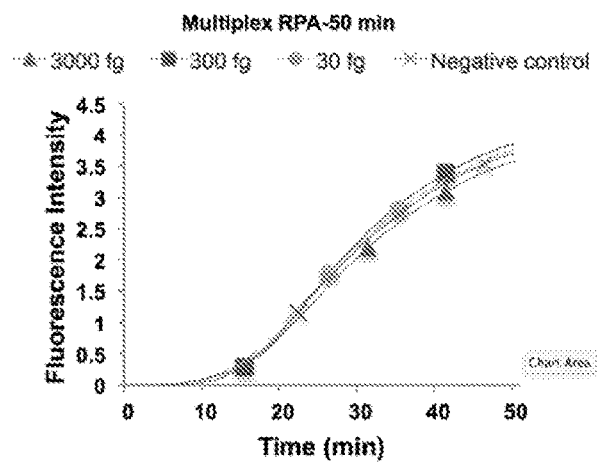
FIG. 11A, FIG. 11B, FIG. 11C, and FIG. 11D compare multiplexed multiple stage isothermal enzymatic amplification and multiplexed RPA of P. falciparum.
Figure 11B:
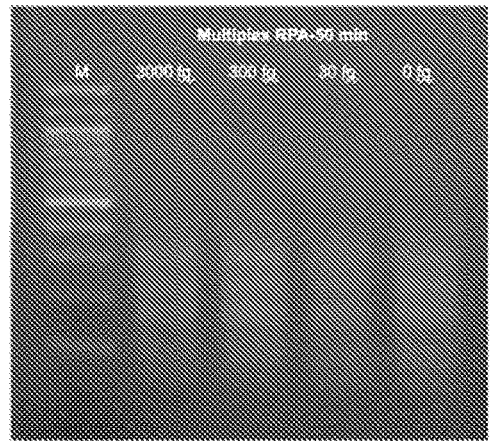
Figure 11C:
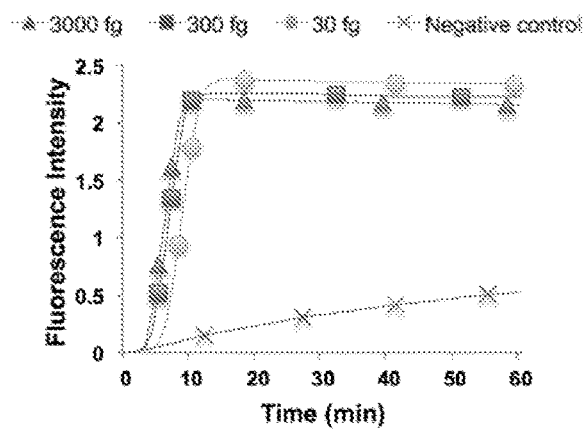
Figure 11D:
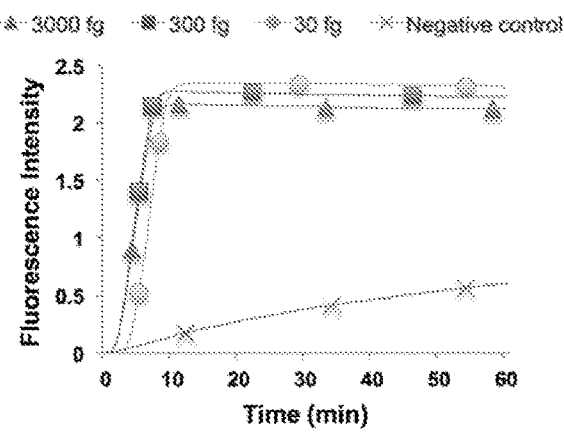

Example 11: Comparison of Multiplex Multiple Stage Isothermal Enzymatic Amplification with Multiplex RPA Next, multiplexed multiple stage isothermal enzymatic amplification was compared with multiplexed RPA (FIG. 11A-11D). The RPA experiments used a multiplexed assay for the amplification of HIV-1 clade B, *P. falciparum*, *S. haematobium*, and *S. mansoni*. Since it is not possible to distinguish among the various targets in the RPA assay when using nonspecific intercalating dye, each sample contained only one target. The results for the multiplexed assay were similar to the results obtained when comparing single-plex multiple stage isothermal enzymatic amplification with single-plex RPA. Briefly, the RPA assay exhibited nonspecific amplification and was less efficient than multiple stage isothermal enzymatic amplification, requiring longer time to saturation (FIGS. 11B and 11A, respectively). In contrast, even in the presence of multiple primer pairs in the first stage of the multiple stage isothermal enzymatic amplification, the selectivity of the second stage of multiple stage isothermal enzymatic amplification discriminated effectively against any nonspecific targets (FIGS. 11C and 11D).

Example 12: Sixteen-Plex Assay

An assay was designed to detect nucleic acid originating from (1) *S. mansoni*, (2) HIV-1 clade B, (3) *S. haematobium*, (4) *P. falciparum*, (5) *S. japonicum*, (6) *Brugia malayi*, (7) *Strongyloides stercoralis*, (8) drug-resistant *Salmonella*, (9) ZIKV-America strain (mex 2-81, Mexico), (10) ZIKV-Africa strain (MR 766, Uganda), (11) HPV-58, (12) HPV-52, (13) HPV-35, (14) HPV-45, (15) HPV-18, and (16) HPV-16. The primers' sequences are listed in Table 1. The targets were both DNA and RNA (HIV-1 and ZIKV), and range from viruses to multicellular metazoans.

FIGS. 12A-12D depict amplification curves of samples containing different template nucleic acids and primers for each of the sixteen sources of nucleic acids identified above. HPV-16 (100 copies) and ZIKV (50 PFU, American strain) (FIG. 12A); HPV-18 (100 copies) and ZIKV (50 PFU, African strain) (FIG. 12B); HIV-1 clade B (100 copies), *P. falciparum* (300 fg DNA), the schistosome *S. japonicum* (1 pg DNA), the filarial nematode *B. malayi* (13 pg DNA), the soil-transmitted nematode *S. stercoralis* (1 pg DNA), and drug resistant *Salmonella* (100 copies) (FIG. 12C); and no targets (negative control) (FIG. 12D). Once again, multiple stage isothermal enzymatic amplification proved to be highly sensitive and specific, with no false positives or negatives. At the tested concentrations, the assay successfully discriminated among various strains of HPV and between American and African strains of the Zika virus.

To examine assay sensitivity and the dependence of the threshold time on target concentration, these experiments were repeated using a dilution series. FIG. 12E depicts the amplification curves obtained with the 16-plex multiple stage isothermal enzymatic amplification assay in the presence of 0, 1, 5, 50, and 500 PFU of the American ZIKV. Note that 1 PFU of ZIKV was detected. When the number of Zika templates was equal to or larger than 5 PFU, the threshold time (the time required for the signal to reach half its saturation value) $T_{1/2}$ was a linear function of the number of target ZIKV (PFU) (FIG. 12F) and data were highly reproducible (with a relative standard deviation in threshold time of 2%). If a 100 µL sample was processed, the detection limit of multiple stage isothermal enzymatic amplification for ZIKV would be better than 50 PFU/mL. This is orders of magnitude lower than the ZIKV concentrations, ranging from 103-106 PFU/mL, in symptomatic Zika-infected patients (Perkasa, A. et al. Isolation of Zika Virus from Febrile Patient, Indonesia. Emerg Infect Dis 22, 924-925 (2016)). Moreover, the data suggest that multiplex multiple stage isothermal enzymatic amplification can genotype HPV strains and, at the target concentrations tested, differentiate the American ZIKV from the African strain.

Example 13: Multiple Stage Isothermal Enzymatic Amplification Performance with Minimally-Prepared Samples Urine Sample Spiked with Zika Virus To reduce test complexity and time, it is occasionally desirable to minimize, or even eliminate, sample preparation. The literature describes rapid tests in which a minimally processed sample is added directly to the reaction volume Such samples are, however, likely to include inhibitors, which may adversely impact nucleic acid amplification, imposing significant limitations on sample volume and, in turn, on assay sensitivity. To assess multiple stage isothermal enzymatic amplification compatibility with rapid sample preparation methods, the 16-plex multiple stage isothermal enzymatic amplification performance of the previous section was examined when urine was added to the reaction volume without nucleic acid extraction.

Figure 13A:
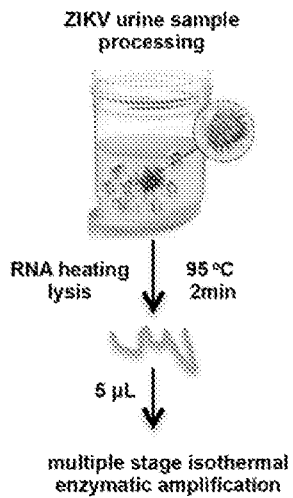
FIG. 13A provides an overview of urine sample processing used prior to multiple stage isothermal enzymatic amplification analysis.
Figure 13B:
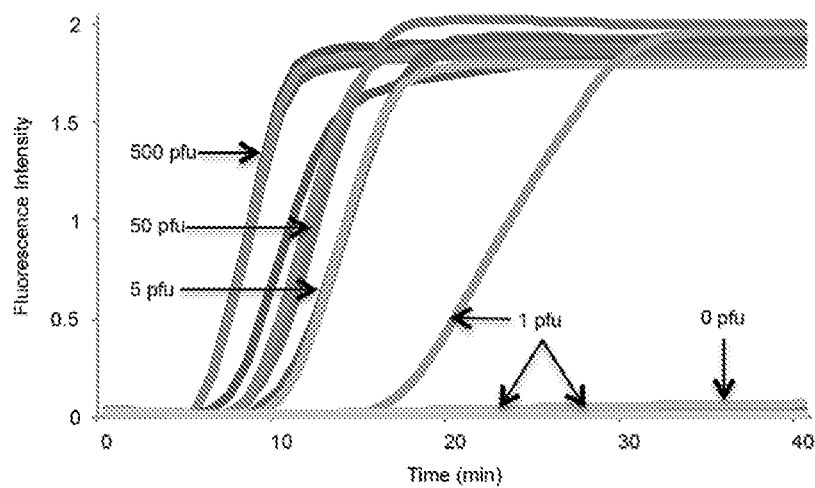
FIG. 13B depicts amplification curves for zika virus nucleic acid obtained from a urine sample.
Figure 13C:
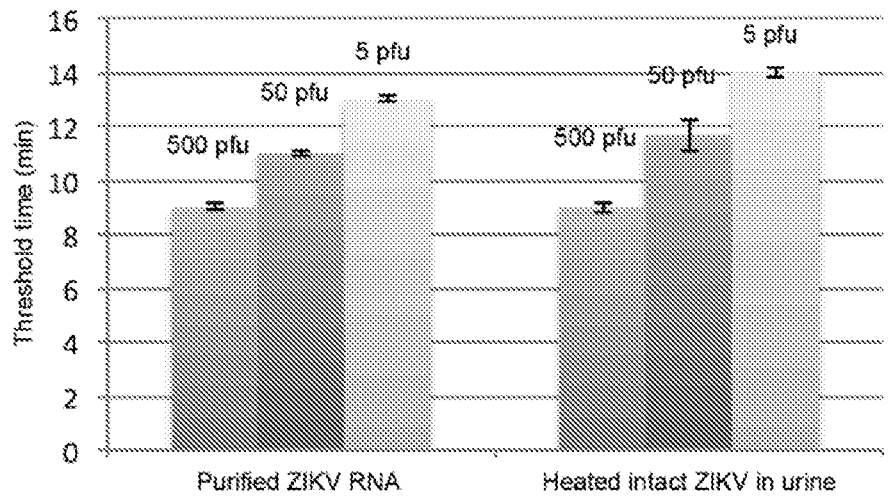
FIG. 13C illustrates threshold times for detecting different amounts of starting Zika virus templates, which confirms the repeatability of detection of heated intact ZIKV in urine by multiple stage isothermal enzymatic amplification is similar to that of purified ZIKV RNA.

A urine sample from a presumably healthy individual was spiked with cultured intact Zika virus. The sample was heated to 95° C. for 2 min. Then, 5 µL of the heated sample was transferred into a 16-plex multiple stage isothermal enzymatic amplification chip (FIG. 13A) and subjected to multiple stage isothermal enzymatic amplification. The resulting amplification curves (FIG. 13B) indicated that multiple stage isothermal enzymatic amplification can detect as few as 5 PFU of ZIKV with good repeatability (N=3). This corresponds to a sensitivity of 103 PFU/mL. The $T_{1/2}$ values and the repeatability of detection of heated intact ZIKV in urine by multiple stage isothermal enzymatic amplification were similar to those for purified ZIKV RNA (FIG. 13C), indicating the robustness and tolerance to inhibitors of multiple stage isothermal enzymatic amplification.

Serum Samples

Additionally, experiments were performed using mouse serum and simulated human serum prepared by separating serum from whole blood with a custom-made, point of care plasma/serum separator (FIG. 14C) as described in Liu, C. et al. A high-efficiency superhydrophobic plasma separator. Lab Chip 16, 553-560, doi:10.1039/c5lc01235j (2016), the contents of which are incorporated herein. Two mice were infected with S. mansoni and the serum was tested 7-weeks after infection. In one experiment, 5 µL serum was added to 45 µL RPA reaction volume. FIG. 14A depicts the corresponding multiple stage isothermal enzymatic amplification curves from these two infected mice and an uninfected mouse (negative control). Both infected mice tested positive and the healthy mouse tested negative. While not being bound to theory, the differences in the threshold times may be due to differences in the number of active S. mansoni in the infected mice. In the second experiment, the same procedure was repeated but the serum volume was doubled to 10 µL, i.e., 10 µL serum was added to 40 µL reaction volume. FIG. 14B depicts the amplification curves. Only the mouse with the higher level of nucleic acid concentration, as reflected by the smaller threshold time in FIG. 14A, presented positive, while the second mouse and the uninfected mouse presented negative. Although the number of targets in the second experiment was double that of the first experiment, inhibitors in the sample apparently reduced polymerase efficiency sufficiently to result in a false negative test for one of the mice. In summary, the experiment indicated that inhibitors in serum adversely impact assay sensitivity, but perhaps can be tolerated when the serum volume does not exceed 10% of the multiple stage isothermal enzymatic amplification reaction volume.

Human Serum

Next, simulated human serum samples were tested by spiking 5 µL (10% of reaction volume) serum with 50, 5, 0.5, and 0 fg of S. mansoni DNA. The serum was separated from whole blood with a custom-made, electricity-free plasma/serum separator (FIG. 14C) as described in Liu, C. et al. A high-efficiency superhydrophobic plasma separator. Lab Chip 16 553-560 (2016). Each sample was then mixed with 45 µL solution containing RPA buffer and primer set 1. The cocktail was subjected to 20 min first-stage RPA followed by single-plex LAMP (FIG. 14D). In parallel, the same sample was amplified using LAMP alone (FIG. 14E). multiple stage isothermal enzymatic amplification successfully detected all samples down to 0.5 fg S. mansoni DNA. LAMP (45 µL buffer+5 µL serum) was less sensitive than multiple stage isothermal enzymatic amplification, providing a signal only for the most DNA-abundant sample (50 fg S. mansoni DNA). When operating with purified samples, multiple stage isothermal enzymatic amplification was typically ten-fold more sensitive than LAMP alone. Since LAMP was more susceptible to contaminants than multiple stage isothermal enzymatic amplification, LAMP was approximately 100-fold less sensitive than multiple stage isothermal enzymatic amplification when operating with serum. Since the first-stage of multiple stage isothermal enzymatic amplification is RPA, multiple stage isothermal enzymatic amplification inherits RPA tolerance to inhibitors. In the multiple stage isothermal enzymatic amplification assay, the original sample were further diluted and target templates were pre-amplified when transferred from the first-stage RPA to the second-stage, reducing the effective concentration of inhibitors and their adverse effects and increase initial effective template concentration for the second-stage LAMP. Thus, multiple stage isothermal enzymatic amplification can operate effectively with crude serum samples, without further purification. Furthermore, serum can be isolated from fresh whole blood by aspirating the supernatant, following blood clotting (without centrifugation) (Rosser, A., Rollinson, D., Forrest, M. & Webster, B. L. Isothermal Recombinase Polymerase amplification (RPA) of *Schistosoma haematobium* DNA and oligochromatographic lateral flow detection. Parasit Vectors 8, 446 (2015)) or with a custom-made plasma/serum separator (Liu, C. et al. A high-efficiency superhydrophobic plasma separator. Lab Chip 16 (2016)).

In summary, when targets are sufficiently abundant in the sample, one can add the crude sample directly into the multiple stage isothermal enzymatic amplification reaction mix for rapid POC diagnostics. Multiple stage isothermal enzymatic amplification benefits from its first stage (RPA) high tolerance to inhibitors. Since the original sample gets further diluted and target templates get pre-amplified when transferred from the first-stage RPA to the second-stage LAMP, the adverse effects of inhibitors are reduced and the initial effective template concentration for the second-stage LAMP is increased. When targets are at low abundance, use of a first-stage multiple stage isothermal enzymatic amplification chamber equipped with a nucleic acid separation membrane at its inlet allows the use of relatively large sample volumes, decoupled from the reaction volume, and enables nucleic acid purification to achieve high sensitivity. Although the serum contains abundance of cell-free DNA, the host DNA does not appear to significantly interfere with the detection.

Whole Blood Samples

Possible interference from human nucleic acids that are present in abundance in whole blood was tested. A multiple stage isothermal enzymatic amplification assay for the detection of HIV RNA, *S. mansoni* DNA, *P. falciparum* DNA, and *S. haematobium* DNA was prepared. The sample consisted of a finger prick of whole blood donated by a presumably healthy individual. The spiked drop (50 µL) was diluted in water in the ratio 1:25 for hypotonic lysis and heated to 99° C. for 5 min. 10 µL of the heated and diluted sample was then spiked with *P. falciparum* DNA (60 fg DNA), HIV RNA (200 copies), and *S. mansoni* (1.5 fg DNA). The sample was spiked after the heating step to prevent RNA degradation (FIG. 15A).

A 10 µL of the diluted and heated blood was added to a 50 µL RPA reaction mix, containing primer pairs for four targets (FIG. 15A). The reaction mix was subjected to a first-stage multiple stage isothermal enzymatic amplification for 15 min. Then, 1 µL portions of RPA products were aliquoted into specific 15 µL LAMP reactors, each storing primers for one of the targets, and incubated at 63° C. FIG. 15B depicts the amplification curves obtained during the incubation. All three targets provided positive signals, while no signal was detected from the *S. haematobium* (negative control) tube. Thus, the assay did not produce any false positives. To further verify that human nucleic acids that are abundant in whole blood do not interfere with the amplification, the process was repeated with a drop of blood that did not contain any targets (negative control). The corresponding second stage amplification curves are depicted in FIG. 15C—all negative. These experiments indicate that although human DNA and possibly RNA are present in large quantities in the sample, they did not adversely affect the amplification process and did not cause any false positives.

Example 14: Comparison of Multiple Stage Isothermal Enzymatic Amplification with IsoPCR and Nested PCR First stage amplification reactions employing an RPA reaction protocol were incubated for 20 minutes. Second stage LAMP reactions were incubated until a detectable amount of amplification product was produced. FIG. 16 shows that the combined time for the RPA and LAMP reactions ranged from 26 min to 36 minutes. FIG. 16 also includes reaction times for the amplification of *Candida glabrata* using nested PCR and isoPCR. FIG. 16 is not a direct comparison between the currently claimed methodology and Nested PCR and isoPCR as different starting nucleic acids are used, but FIG. 16 does illustrate the fast reaction times of the currently claimed invention.

Example 15: Use of Sequence-Specific Endonucleases to Enrich Nucleic Acids of Interest Traces of low copy nucleic acids (NA) in clinical samples provide vital clues of disease states, infections, and contamination, and inform on therapy. Detecting such information-rich, low-abundance NA sequences, which often exist within a large excess of normal (wild-type WT) NA, poses persistent technical challenges in biology, biotechnology and medicine. These include, among other things, cancer, prenatal diagnosis, infectious diseases, organ transplants, and forensics.

Removing the vast majority of normal, masking DNA that does not provide the desired or necessary clinical information may enable enriching rare DNA to reveal the wealth of information contained in altered DNA. For example, mutations in the KRAS gene can cause normal cells to become cancerous and induces resistance to certain cancer drugs. KRAS mutations are common in colon cancer, lung cancer, and pancreatic cancer and define distinct molecular subsets of the disease. Detection of these mutations may facilitate early cancer diagnostics and guide therapy. Because KRAS mutations may be present in less than 0.01% of DNA molecules during the early stage of disease, detection of abnormal DNA presents a significant challenge for current nucleic acid detection methods.

Many pathogens responsible for infectious diseases include strains that contain small differences, e.g., single-base pair alterations, in nucleic acid sequences. The ability to eliminate nucleic acids with certain sequences may enable one to unmask the presence of the strains of interest.

Because the two-stage amplification disclosed herein is carried out at relatively low temperatures (lower than polymerase chain reaction PCR), it provides one with the opportunity to incorporate restriction enzymes or slicing proteins, such as Cas9 (CRISPR associated protein 9) and TtAgo (Argonaute of the bacterium *Thermus thermophilus*) in the first stage reaction and/or the second stage reaction to suppress the amplification of unwanted selected sequences. Cas9 and Ttago are highly-sequence specific endonuclease complexes that cut targeted nucleic acids with high precision. They can be programmed with a synthetic guide to target a subpopulation of nucleic acids in a heterogeneous mixture of nucleic acids. Cas9 is an RNA-guided DNA cleaving enzyme. Cas9 unwind and interrogate DNA. When the DNA substrate has a sequence complementary to 20 base pairs of the guide RNA adjacent to a protospacer adjacent motif (PAM) site, Cas9 cleaves the DNA 3-4 nucleotides upstream of the PAM sequence. TtAgo is typically introduced with 5'-phosphorylated DNA guides, 13 to 25 nucleotides in length, that guide TtAgo to cleave complementary DNA strands.

FIGS. 17A and 17B exemplify two options for removing unwanted wildtype KRAS DNA, one option utilizes the enzyme Cas9, and the other uses the enzyme TtAgo. FIG. 17A describes the use of Cas9 to detect a mutation in the last two nucleotides (GG) of PAM site (NGG), where N stands for any nucleotide. Such a single-base alternation suppresses cleavage of Cas9, such as KRAS G12D (c.35G>A). Cas9 with the RNA guide described in the figure cleaves wildtype DNA. Subsequent DNA-amplification will enrich the fraction of DNA mutants in the wildtype/mutant mixture. Because Cas9 operates optimally at 37° C., it is compatible with the first-stage of RAMP. It can, however, only address the mutations at the PAM sites.

Alternatively, one can use the enzyme TtAgo to cut wildtype DNA (FIG. 17B). To this end, one may design the guide DNA to be complementary with a non-mutated sequence in the wildtype DNA, enabling TtAgo to cleave the wildtype DNA, while mutated DNA will fail to hybridize with the guide DNA. Thus DNA-amplification will enrich only mutant DNA. TtAgo has the advantage that it is not limited to the PAM sites. Mutations at any positions can be designed for enrichment. TtAgo cleavage activity may be strongly temperature-dependent: whereas ssDNA is cleaved at temperatures ≥20° C., dsDNA is only cleaved at temperatures ≥65° C. [5]. To overcome this limitation, it is possible to replace the first stage RPA with another, higher temperature isothermal amplification method such as Helicase-dependent amplification (HDA), LAMP, or NASBA as the first stage of RAMP.

FIGS. 18A and 18B exemplify two options for differentiating ZIKV African and American strains. FIG. 18A describes the use of Cas9 to differentiate America ZIKV strain from Africa ZIKV strain. One may identify a single-nucleotide polymorphism (SNP) site that differentiate between these two Zika strains. Here, one may focus on the PAM site present in the African stain and absent in the American strain. This allows one to incorporate into the assay specific cleavage of African strain and differentiate the two strains with good specificity.

FIG. 18B illustrated the use of TtAgo to differentiate America and Africa ZIKV strains. One may identify regions with SNP sites that can affect DNA hybridization to these two strains. One may design the guide DNA to be complementary with the Africa strain, but not with the America strain. The better hybridization between the guide DNA and the Africa strain amplicons or RNA leads to a specific cleavage of the Africa strain. Because TtAgo operates optimally at temperatures ≥65° C., the differentiation assay can be carried out concurrently with LAMP (in a single process) or after LAMP amplification.

Those skilled in the art will appreciate that numerous changes and modifications can be made to the preferred embodiments of the disclosed methods and that such changes and modifications can be made without departing from the spirit of the invention. It is, therefore, intended that the appended claims cover all such equivalent variations as fall within the true spirit and scope of the invention.

The disclosures of each patent, patent application, and publication cited or described in this document are hereby incorporated herein by reference, in its entirety.

EMBODIMENTS

The following list of embodiments is intended to complement, rather than displace or supersede, the previous descriptions.

Embodiment 1

Multiple stage nucleic acid amplification comprising:
a first recombinase polymerase amplification reaction performed at a substantially isothermal temperature to generate a first amplification product, the nucleic acid serving as a template for the recombinase polymerase amplification reaction; and
at least one subsequent loop-mediated amplification reaction performed at a substantially isothermal temperature to generate a second amplification product in an amount sufficient for recovery, testing, or characterization, the first amplification product serving as a template for the loop-mediated isothermal reaction.

Embodiment 2

The multiple stage nucleic acid amplification of embodiment 1, wherein the substantially isothermal temperature of the first recombinase polymerase amplification reaction differs from the substantially isothermal temperature of the second stage.

Embodiment 3

The multiple stage nucleic acid amplification of embodiment 1 or 2, wherein the substantially isothermal temperature of the first recombinase polymerase amplification reaction is in a range of about 25° C. to about 65° C.

Embodiment 4

The multiple stage nucleic acid amplification of any one of embodiments 1 to 3, wherein the substantially isothermal temperature of the at least one loop-mediated amplification reaction is in a range of about 55° C. to about 80° C.

Embodiment 5

The multiple stage nucleic acid amplification of any one of embodiments 1 to 4, wherein at least one of the amplification reactions employs a reverse transcriptase.

Embodiment 6

The multiple stage nucleic acid amplification of any one of embodiments 1 to 5, wherein the first amplification product is essentially a single amplicon.

Embodiment 7

The multiple stage nucleic acid amplification of any one of embodiments 1 to 5, wherein the first amplification product is a plurality of amplicons.

Embodiment 8

The multiple stage nucleic acid amplification of any one of embodiments 1 to 8, wherein the first amplification product serves as a template for a plurality of subsequent loop-mediated amplification reactions.

Embodiment 9

The multiple stage nucleic acid amplification of embodiment 8, wherein at least some of the second stage reactions generate a plurality of amplicons.

Embodiment 10

The multiple stage nucleic acid amplification of any one of embodiments 1 to 9, wherein the nucleic acid is a region of a genome of an infectious agent or a genetic marker.

Embodiment 11

The multiple stage nucleic acid amplification of embodiment 10, wherein the infectious agent is human immunodeficiency virus, *Schistosoma mansoni, Schistosoma haematobium, Plasmodium falciparum, S. japonicum, Brugia malayi, Strongyloides stercoralis*, drug-resistant *Salmonella*, ZIKV-America strain (mex 2-81, Mexico), ZIKV-Africa strain (MR 766, Uganda), HPV-58, HPV-52, HPV-35, HPV-45, HPV-18, HPV-16, or a combination thereof.

Embodiment 12

The multiple stage nucleic acid amplification of embodiment 10, wherein the nucleic acid is associated with food borne pathogens, agents of bioterror, or environmental agents.

Embodiment 13

Multiple stage nucleic acid amplification comprising:
a first substantially isothermal amplification reaction on the nucleic acid to generate a first amplification product; and
at least one substantially isothermal amplification reaction on the first amplification product to generate at least one second amplification product in an amount sufficient for recovery, testing, or characterization.

Embodiment 14

The multiple stage nucleic acid amplification of embodiment 13, wherein at least one reaction employs a reverse transcriptase.

Embodiment 15

The multiple stage nucleic acid amplification of embodiment 13 or 14, wherein each reaction employs an enzymatic system to amplify nucleic acids.

Embodiment 16

The multiple stage nucleic acid amplification of embodiment 15, wherein each amplification reaction is performed at a substantially isothermal temperature matched to the enzyme system in the reaction.

Embodiment 17

The multiple stage nucleic acid amplification of any one of embodiments 13 to 16, wherein at least one of the reactions is performed at a temperature in the range of about 25° C. to about 65° C.

Embodiment 18

The multiple stage nucleic acid amplification of any one of embodiments 13 to 17, wherein at least one of the reactions is performed at a temperature in the range of about 35° C. to about 45° C.

Embodiment 19

The multiple stage nucleic acid amplification of any of embodiments 13 to 18, wherein at least one of the reactions is a recombinase polymerase reaction.

Embodiment 20

The multiple stage nucleic acid amplification of any one of embodiments 13 to 19, wherein at least one of the reactions is performed at a temperature in the range of about 55° C. to about 99° C.

Embodiment 21

The multiple stage nucleic acid amplification of any one of embodiments 13 to 20, wherein at least one of the reactions is performed at a temperature in the range of about 55° C. to about 80° C.

Embodiment 22

The multiple stage nucleic acid amplification of any of embodiments 13 to 21, wherein at least one of the reactions is a loop-mediated isothermal amplification reaction.

Embodiment 23

The multiple stage nucleic acid amplification of any of embodiments 13 to 22, wherein the first substantially isothermal amplification reaction is a recombinase polymerase reaction and the second substantially isothermal amplification reaction is a loop-mediated isothermal amplification reaction.

Embodiment 24

The multiple stage nucleic acid amplification of any one of embodiments 13 to 22, wherein at least one of the reactions is a nucleic acid sequence-based amplification.

Embodiment 25

The multiple stage nucleic acid amplification of any one of embodiments 13 to 22 or 24, wherein at least one of the reactions is a helicase dependent amplification.

Embodiment 26

The multiple stage nucleic acid amplification of any one of embodiments 13 to 22 or 24 to 25, wherein the first substantially isothermal amplification reaction is a multiple displacement amplification reaction.

Embodiment 27

The multiple stage nucleic acid amplification of any one of embodiments 13 to 26, wherein the first amplification product is essentially a single amplicon.

Embodiment 28

The multiple stage nucleic acid amplification of any one of embodiments 13 to 26, wherein the first amplification product is a plurality of amplicons.

Embodiment 29

The multiple stage nucleic acid amplification of any one of embodiments 13 to 28, wherein the first amplification product serves as a template for a plurality of second substantially isothermal amplification reactions.

Embodiment 30

The multiple stage nucleic acid amplification of embodiment 29, wherein at least some of the second substantially isothermal amplification reactions generate a plurality of amplicons.

Embodiment 31

The multiple stage nucleic acid amplification of any one of embodiments 13 to 30, wherein the second amplification product comprises one or more amplicons.

Embodiment 32

The multiple stage nucleic acid amplification of embodiment 31, wherein the second amplification product is essentially one amplicon.

Embodiment 33

The multiple stage nucleic acid amplification of embodiment 31, wherein the second amplification product comprises between two and ten amplicons.

Embodiment 34

The multiple stage nucleic acid amplification of embodiment 31, wherein the second amplification product further comprises more than ten amplicons.

Embodiment 35

The multiple stage nucleic acid amplification of any of the previous embodiments, further comprising one or more additional isothermal amplification reactions.

What is claimed is:

1. A multiple stage nucleic acid amplification, comprising:
   a) first recombinase polymerase amplification reaction performed on a nucleic acid at a substantially isothermal temperature to generate a first amplification product; and
   b) at least one subsequent loop-mediated amplification reaction performed on the first amplification product at a substantially isothermal temperature to generate at least one second amplification product in an amount sufficient for recovery, testing, or characterization
   wherein the ratio of the first amplification product from step (a) used in the at least one subsequent loop-mediated amplification reaction of step (b) is 1:15.

2. The multiple stage nucleic acid amplification of claim 1, wherein the substantially isothermal temperature of the first recombinase polymerase amplification reaction differs from the substantially isothermal temperature of the at least one subsequent loop-mediated amplification reaction.

3. The multiple stage nucleic acid amplification of claim 1, wherein at least one of the first recombinase polymerase amplification reaction and the at least one subsequent loop-mediated amplification reaction employs a reverse transcriptase.

4. The multiple stage nucleic acid amplification of claim 1, wherein the first amplification product is essentially a single amplicon.

5. The multiple stage nucleic acid amplification of claim 1, wherein the first amplification product is a plurality of amplicons.

6. The multiple stage nucleic acid amplification of claim 1, wherein the first amplification product serves as a template for a plurality of subsequent loop-mediated amplification reactions.

7. The multiple stage nucleic acid amplification of claim 1, wherein the nucleic acid is a region of a genome of an infectious agent or a genetic marker.

8. The multiple stage nucleic acid amplification of claim 7, wherein the infectious agent is human immunodeficiency virus, *Schistosoma mansoni*, *Schistosoma haematobium*, *Plasmodium falciparum*, *S. japonicum*, *Brugia malayi*, *Strongyloides stercoralis*, drug-resistant *Salmonella*, ZIKV-America strain (mex 2-81, Mexico), ZIKV-Africa strain (MR 766, Uganda), HPV-58, HPV-52, HPV-35, HPV-45, HPV-18, HPV-16, or a combination thereof.

9. The multiple stage nucleic acid amplification of claim 7, wherein the nucleic acid is associated with food borne pathogens, agents of bioterror, or environmental agents.

10. A multiple stage nucleic acid amplification, comprising:
    a) first substantially isothermal amplification reaction performed on a nucleic acid to generate a first amplification product; and
    b) at least one substantially isothermal amplification reaction performed on the first amplification product to generate at least one second amplification product in an amount sufficient for recovery, testing, or characterization,
    wherein the ratio of the first amplification product from step (a) used in the at least one amplification reaction of step (b) is 1:15.

11. The multiple stage nucleic acid amplification of claim 10, wherein the temperature of step (a) differs from the temperature of step (b).

12. The multiple stage nucleic acid amplification of claim 10, wherein at least one of the first amplification reaction from step (a) and the at least one amplification reaction from step (b) is performed at a temperature in the range of about 25° C. to about 65° C.

13. The multiple stage nucleic acid amplification of claim 10, wherein at least one of the first amplification reaction from step (a) and the at least one amplification reaction from step (b) is a recombinase polymerase reaction, a loop-mediated isothermal amplification reaction, a nucleic acid sequence-based amplification, a helicase dependent amplification, or a multiple displacement amplification reaction.

14. The multiple stage nucleic acid amplification of claim 10, wherein at least one of the first amplification reaction from step (a) and the at least one amplification reaction from step (b) is performed at a temperature in the range of about 55° C. to about 99° C.

15. The multiple stage nucleic acid amplification of claim 10, wherein the first amplification reaction from step (a) is a recombinase polymerase reaction and the second amplification reaction from step (b) is a loop-mediated isothermal amplification reaction.

16. The multiple stage nucleic acid amplification of claim 10, wherein the first amplification product is essentially a single amplicon.

17. The multiple stage nucleic acid amplification of claim 10, wherein the first amplification product is a plurality of amplicons.

18. The multiple stage nucleic acid amplification of claim 10, wherein the first amplification product serves as a template for a plurality of second substantially isothermal amplification reactions.

19. The multiple stage nucleic acid amplification of claim 10, wherein the second amplification product comprises one or more amplicons.

20. The multiple stage nucleic acid amplification of claim 10, further comprising one or more additional isothermal amplification reactions.

* * * * *

UNITED STATES PATENT AND TRADEMARK OFFICE
CERTIFICATE OF CORRECTION

| | |
|---|---|
| PATENT NO. | : 11,118,206 B2 |
| APPLICATION NO. | : 16/068560 |
| DATED | : September 14, 2021 |
| INVENTOR(S) | : Bau et al. |

It is certified that error appears in the above-identified patent and that said Letters Patent is hereby corrected as shown below:

In the Specification

In Detailed Description of Illustrative Embodiments

Under Column No. 7, Line no. 9, Replace, "Notomi  et al." with -- Notomi et al. --

Under Column No. 9, Line no. 51, Replace, "anthraces" with -- anthracis --

In Examples

Under Column No. 15, Line no. 53, Replace, "20 min 1 µL" with -- 20 min. 1 µL --

Under Column No. 15, Line no. 61, Replace, "Calif." with -- CA --

Under Column No. 21, Line no. 57, Replace, "$T_{1/2} \pm s.d.$" with -- $T_{1/2} \pm s.d.$ --

Signed and Sealed this
Fifth Day of July, 2022

Katherine Kelly Vidal
*Director of the United States Patent and Trademark Office*

```
                         SEQUENCE LISTING

<160> NUMBER OF SEQ ID NOS: 99

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
attatcagaa ggagccacc                                                  19

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
catcctattt gttcctgaag g                                               21

<210> SEQ ID NO 3
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cagcttcctc attgatggtt tcttttttaac accatgctaa acacagt                  47

<210> SEQ ID NO 4
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tgttgcacca ggccagataa ttttgtactg gtagttcctg ctatg                     45
```

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tttaacattt gcatggctgc ttgat                                         25

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gagatccaag gggaagtga                                                19

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ttatcgtcta tagtacggta gg                                            22

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
atactttaac ccccaccaa                                                19

<210> SEQ ID NO 9
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gccaagtaga gactacaaac atctttgggt aaggtagaaa atgttgt                 47

<210> SEQ ID NO 10
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
agaagtgttt aacttgatga aggggaaaca aaaccgaaac cacta                   45

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
ctgcacgaaa tacagaat                                                      18

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
gtatgttctg tcctcttg                                                      18

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
tcgcttctaa cggtgaac                                                      18

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
aattgatagt atcagctatc catag                                              25

<210> SEQ ID NO 15
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
ggtggaacac attgtttcat ttgatctcat tccaatggaa ccttg                        45

<210> SEQ ID NO 16
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
gtttgcttct aacattccac ttgcccgttt tgaccggtca tt                           42

<210> SEQ ID NO 17

```
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17 cactataccct taccaatcta tttgaacttg                                        30

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tggacgtaac ctccaggc                                                      18

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ctttctaagc ccgcgata                                                      18

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gcgcattaca cttggtct                                                      18

<210> SEQ ID NO 21
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21 taccectaac ttcgtggtct ccccccctta ttttagggtg c                            41

<210> SEQ ID NO 22
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ctccctatat aacatggcga gtaagactat gaaatcagtg tttttcgg                     48

<210> SEQ ID NO 23
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ggtgcgcttt gttttccgt                                                    19

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
accatgtgta aagcgcgtca aa                                                22

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gcgcataaat tcatcagc                                                     18

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gcaaaactta attacaaaag cg                                                22

<210> SEQ ID NO 27
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gcttttttta gtagttttgg cacttcttac attagacaag gaaattgg                    48

<210> SEQ ID NO 28
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gaaaytaatt gactatgtta cgtgcacaac acaatatacg accagc                      46

<210> SEQ ID NO 29
<211> LENGTH: 23
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 29
aattaraatt aaaattgata aat                                           23

<210> SEQ ID NO 30
<211> LENGTH: 11
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
attgtaccag t                                                        11

<210> SEQ ID NO 31
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
gtgtaggctg gcgtagt                                                  17

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
tttcaatttt agcttaggac c                                             21

<210> SEQ ID NO 33
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
gctactatca ccaagatctg cacgcattga aggttataag cgtaag                  46

<210> SEQ ID NO 34
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
acacaagtga gaatcttgtg gacctaactc acagtcaaat gatgt                   45

<210> SEQ ID NO 35
<211> LENGTH: 22
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 35
cgaagtggaa aagggtttca cg                                              22

<210> SEQ ID NO 36
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
acttctagtg gtgttcgtca ggcttgt                                         27

<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ctaactttgg tgccgaatta agcca                                           25

<210> SEQ ID NO 38
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
agggaaatca gacgatgaca atgctatctc catttttatt taa                       43

<210> SEQ ID NO 39
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
tttgaccacc ttaaacatga atgaagtaac attttacatt tgga                      44

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
tctaaaagta tgtcaatgat aa                                              22

<210> SEQ ID NO 41
<211> LENGTH: 24
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 41
aagcatgctt gggatgcgat tctc                                              24

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
tgcaaccatt aaaactggcg                                                   20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
tggagcgttt tctcctgaac                                                   20

<210> SEQ ID NO 44
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
tacgggcttc ccttcgcgat agtggattac ggttccgcag a                           41

<210> SEQ ID NO 45
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gccgaagcct atggcgtgaa gtggctggca tccatgtt                               38

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
cccaggcata atcttttttgt tcgt                                             24

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 47
atccagcgtt attgatatgg cc					22

<210> SEQ ID NO 48
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
agttcaagga cgcacatgc					19

<210> SEQ ID NO 49
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
aacgctgcgr tacacaag					18

<210> SEQ ID NO 50
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gcctcyagag ctccagcaag aggcaaactg tcgtggttc					39

<210> SEQ ID NO 51
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gtgcaaaggg aaggctgtcc tcgagtatga cacgcccttc aa					42

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ctgctccttc ttgactccct a					21

<210> SEQ ID NO 53
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
tggccacttg aaatgtcgc                                                    19

<210> SEQ ID NO 54
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gaaggagccg ttcacacg                                                     18

<210> SEQ ID NO 55
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
cctgcatact gcacctcc                                                     18

<210> SEQ ID NO 56
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
ggcggcattt caaatggcca gctcgctgga gctctagagg                             40

<210> SEQ ID NO 57
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
tattccttgt gcactgcggc atgactgttc catgcagtgt t                           41

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
cctttgcacc atccatctca g                                                 21

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ttcacattca ccaaggtccc a                                              21

<210> SEQ ID NO 60
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
caaattattt tcctacacct agtgg                                          25

<210> SEQ ID NO 61
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gtcataacgt ctgcagttaa gg                                             22

<210> SEQ ID NO 62
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
gtggccctgt gctcgttgtc tatggttacc tctgatgcc                           39

<210> SEQ ID NO 63
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
cacgcagtac aaatatgtca ccccatgtcg taggtactcc                          40

<210> SEQ ID NO 64
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
gctgccatat ctacttcaga aactaca                                        27

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65

-continued tgtattctcc ctctccaagt g                                               21

<210> SEQ ID NO 66
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
gaatatagga cataacatct gcag                                            24

<210> SEQ ID NO 67
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
gccagcaaac accattgtta ctctattgtt acctctgact ccc                       43

<210> SEQ ID NO 68
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
accactcgca gtaccaattt aaccctcaac atgtctgcta tactgc                    46

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
accctgtgcc ttatgtaacc                                                 20

<210> SEQ ID NO 70
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
cctataggtg aacattggg                                                  19

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
ggatatttgc aaatggaact g                                         21

<210> SEQ ID NO 72
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
gtttagtaac tccaaaggag gacaaaggca caccttgtaa tgc                 43

<210> SEQ ID NO 73
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
gggacatggt agacacagga catatatcta ggggaacatc ac                  42

<210> SEQ ID NO 74
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
cattctcctg cttttacctg gt                                        22

<210> SEQ ID NO 75
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
gaaacacaac gtttggtttg ggc                                       23

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
gtgctcacca atagcaggta c                                         21

<210> SEQ ID NO 77
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
taaaatggat ggccacttag gccggtatgg aaattggtcg tgggc               45

<210> SEQ ID NO 78
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
ggatgataca gaaagtgctc aaaatacaca gctgtgtttg c                          41

<210> SEQ ID NO 79
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
caatacctaa aggctgcc                                                    18

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
gccactgtac aaagcagtgc                                                  20

<210> SEQ ID NO 81
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
tgaatgtatg tcataacatc agctg                                            25

<210> SEQ ID NO 82
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
attattgtgg ccctgcgcac gttctatggt aacctcagaa tccc                       44

<210> SEQ ID NO 83
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
accactcgta gcactaacat gactcgccat gacgaaggta ttcct                      45

<210> SEQ ID NO 84
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
gctgaggtta aaaggaaag caca                                           24

<210> SEQ ID NO 85
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
gacgtgagca gatgtttgt                                                19

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
ccattgttat gaccttgtgc                                               20

<210> SEQ ID NO 87
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
ggataactgc agtattaccg gacctagggc tggaaaactt gg                      42

<210> SEQ ID NO 88
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
tccaactcct agtggctcta tagcgctgta gccaataagg c                       41

<210> SEQ ID NO 89
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
cctcagaatc acaattattt aataagcc                                      28

```
<210> SEQ ID NO 90
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
cgaggttgat ggtgttcaaa ta                                             22

<210> SEQ ID NO 91
<211> LENGTH: 47
<212> TYPE: DNA
<213> ORGANISM: Unknown
<220> FEATURE:
<223> OTHER INFORMATION: Description of Unknown:
      KRAS oligonucleotide

<400> SEQUENCE: 91
ataaacttgt ggtagttgga gctggtggcg taggcaagag tgccttg                  47

<210> SEQ ID NO 92
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
ataaacttgt ggtagttgga gctgatggcg taggcaagag tgccttg                  47

<210> SEQ ID NO 93
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
tctacgccac cagctccaa                                                 19

<210> SEQ ID NO 94
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
cgucgucguu cuggggagcc                                                20

<210> SEQ ID NO 95
<211> LENGTH: 45
<212> TYPE: DNA
<213> ORGANISM: Zika virus

<400> SEQUENCE: 95
aggcaaactg tcgtggttct agggagtcaa gaaggagcag ttcac                    45

<210> SEQ ID NO 96
<211> LENGTH: 45
<212> TYPE: DNA
<213> ORGANISM: Zika virus
```

```
<400> SEQUENCE: 96
aggcaaaccg tcgtcgttct ggggagccag gaaggagccg ttcac              45

<210> SEQ ID NO 97
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
tctccttcct ggctcccca                                           19

<210> SEQ ID NO 98
<211> LENGTH: 45
<212> TYPE: DNA
<213> ORGANISM: Zika virus

<400> SEQUENCE: 98
caaactgtcg tggttctagg gagtcaagaa ggagcagttc acacg              45

<210> SEQ ID NO 99
<211> LENGTH: 45
<212> TYPE: DNA
<213> ORGANISM: Zika virus

<400> SEQUENCE: 99
caaactgtcg tggttctggg gagccaggaa ggagcagttc acacg              45
```